United States Patent
Helson et al.

(10) Patent No.: US 10,449,193 B2
(45) Date of Patent: *Oct. 22, 2019

(54) PROTECTIVE EFFECT OF DMPC, DMPG, DMPC/DMPG, LYSOPG AND LYSOPC AGAINST DRUGS THAT CAUSE CHANNELOPATHIES

(71) Applicant: SignPath Pharma Inc., Quakertown, PA (US)

(72) Inventors: Lawrence Helson, Quakertown, PA (US); George M. Shopp, Boulder, CO (US); Annie Bouchard, Stoke (CA); Muhammed Majeed, East Windsor, NJ (US)

(73) Assignee: Signpath Pharma Inc., Sandy, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 15/297,901

(22) Filed: Oct. 19, 2016

(65) Prior Publication Data

US 2017/0035887 A1 Feb. 9, 2017

Related U.S. Application Data

(63) Continuation-in-part of application No. 14/729,940, filed on Jun. 3, 2015, now Pat. No. 10,258,691, and a continuation-in-part of application No. 14/575,644, filed on Dec. 18, 2014, and a continuation-in-part of application No. 15/068,300, filed on Mar. 11, 2016, which is a continuation of application No. 14/268,376, filed on May 2, 2014, now Pat. No. 9,682,041, which is a continuation of application No. 13/487,233, filed on Jun. 3, 2012, now Pat. No. 8,753,674.

(60) Provisional application No. 62/007,244, filed on Jun. 3, 2014, provisional application No. 61/917,426, filed on Dec. 18, 2013, provisional application No. 61/493,257, filed on Jun. 3, 2011.

(51) Int. Cl.
| | | |
|---|---|---|
| *A61K 31/506* | (2006.01) | |
| *A61K 45/06* | (2006.01) | |
| *A61K 9/127* | (2006.01) | |
| *A61K 31/20* | (2006.01) | |
| *A61K 31/23* | (2006.01) | |
| *A61K 31/683* | (2006.01) | |
| *A61K 31/685* | (2006.01) | |
| *G01N 33/50* | (2006.01) | |
| *G01N 33/68* | (2006.01) | |

(52) U.S. Cl.
CPC .......... *A61K 31/506* (2013.01); *A61K 9/127* (2013.01); *A61K 31/20* (2013.01); *A61K 31/23* (2013.01); *A61K 31/683* (2013.01); *A61K 31/685* (2013.01); *A61K 45/06* (2013.01); *G01N 33/5008* (2013.01); *G01N 33/6872* (2013.01); *G01N 33/6887* (2013.01); *G01N 2800/32* (2013.01)

(58) Field of Classification Search
None
See application file for complete search history.

(56) References Cited

U.S. PATENT DOCUMENTS

| | | |
|---|---|---|
| 4,812,312 A | 3/1989 | Lopez-Berestein et al. |
| 5,023,087 A | 6/1991 | Yao-Young |
| 5,679,864 A | 10/1997 | Krackov et al. |
| 6,143,276 A | 11/2000 | Unger |
| 6,143,321 A * | 11/2000 | Needham ............. A61K 9/1075 424/1.21 |
| 6,787,132 B1 | 9/2004 | Gabison et al. |
| 6,946,475 B1 | 9/2005 | Lloyd |
| 7,060,733 B2 | 6/2006 | Pandol et al. |
| 7,067,159 B2 | 6/2006 | Katz et al. |
| 7,507,864 B2 | 3/2009 | Miller et al. |
| 7,674,820 B2 | 3/2010 | Fedida et al. |
| 7,723,515 B1 | 5/2010 | Dimauro |
| 7,871,609 B2 | 1/2011 | Ziff et al. |
| 7,968,115 B2 | 6/2011 | Kurzrock et al. |
| 8,062,663 B2 | 11/2011 | Wang et al. |
| 8,153,172 B2 | 4/2012 | Antony |
| 8,202,839 B1 | 6/2012 | Sung |
| 8,207,219 B2 | 6/2012 | Fedida et al. |
| 8,642,074 B2 * | 2/2014 | Mei ........................ A61K 9/127 424/450 |
| 8,747,890 B2 | 6/2014 | Helson |
| 8,753,674 B2 | 6/2014 | Helson |
| 9,138,411 B2 | 9/2015 | Ranjan et al. |

(Continued)

FOREIGN PATENT DOCUMENTS

| | | |
|---|---|---|
| CA | 2584279 A1 | 4/2005 |
| CN | 104758255 | 7/2015 |

(Continued)

OTHER PUBLICATIONS

Van Dijck et al (Influence of Ca2+ and Mg2+ on the Thermotropic Behaviour and Permeability Properties of Liposomes Prepared From Dimyristoyl Phosphatidylglycerol and Mixtures of Dimyristoyl Phosphatidylglycerol and Dimyristoyl Phosphatidylcholine. Biochim Biophys Acta 406 (4), 465-478. Nov. 3, 1975).*

(Continued)

*Primary Examiner* — Jake M Vu
(74) *Attorney, Agent, or Firm* — Edwin S. Flores; Chalker Flores, LLP

(57) ABSTRACT

The present invention includes compositions and methods for preventing one or more cardiac channelopathies or conditions resulting from irregularities or alterations in cardiac patterns caused by an active agent or a drug in a human or animal subject comprising: an amount of a lyso-phosphatidylglycerol adapted for oral administration effective to reduce or prevent one or more cardiac channelopathies or conditions resulting from irregularities or alterations in cardiac patterns caused by the active agent or drug.

18 Claims, 4 Drawing Sheets

(56) References Cited

U.S. PATENT DOCUMENTS

| | | |
|---|---|---|
| 2001/0051184 A1 | 12/2001 | Heng |
| 2002/0048598 A1 | 4/2002 | Malik |
| 2002/0110586 A1* | 8/2002 | Madden ............... A61K 9/127 424/450 |
| 2005/0101674 A1 | 5/2005 | Maurer et al. |
| 2005/0181036 A1 | 8/2005 | Aggarwal et al. |
| 2005/0233970 A1 | 10/2005 | Garnick |
| 2005/0266067 A1 | 12/2005 | Sengupta et al. |
| 2006/0067998 A1 | 3/2006 | Kurzrock et al. |
| 2006/0147512 A1 | 7/2006 | Sabin |
| 2006/0269595 A1 | 11/2006 | Madden |
| 2007/0048284 A1 | 3/2007 | Donahue et al. |
| 2008/0075671 A1 | 3/2008 | Di Mauro |
| 2008/0103213 A1 | 5/2008 | Kurzrock et al. |
| 2008/0107749 A1 | 5/2008 | Maitra et al. |
| 2008/0138400 A1 | 6/2008 | Kurzrock et al. |
| 2008/0253961 A1 | 10/2008 | Braden et al. |
| 2008/0255464 A1 | 10/2008 | Vincent |
| 2009/0143433 A1 | 6/2009 | Hendrix |
| 2009/0246770 A1 | 10/2009 | Levy |
| 2009/0291134 A1 | 11/2009 | Ateeq et al. |
| 2009/0317387 A1 | 12/2009 | Paton et al. |
| 2009/0324703 A1 | 12/2009 | Frautschy et al. |
| 2010/0004549 A1 | 1/2010 | Kohls et al. |
| 2010/0048957 A1 | 2/2010 | Kim |
| 2010/0068251 A1* | 3/2010 | Ali ........................ A61K 9/127 424/450 |
| 2010/0093873 A1 | 4/2010 | Goldfischer |
| 2010/0120890 A1 | 5/2010 | Fedida |
| 2010/0151000 A1 | 6/2010 | Thomas et al. |
| 2010/0179103 A1 | 7/2010 | Desai |
| 2010/0239552 A1 | 9/2010 | Mayoux et al. |
| 2010/0240581 A1 | 9/2010 | Tortoriello et al. |
| 2010/0291043 A1 | 11/2010 | Medin et al. |
| 2011/0117186 A1 | 5/2011 | Helson |
| 2011/0200665 A1* | 8/2011 | Mei ........................ A61K 9/127 424/450 |
| 2011/0229555 A1 | 9/2011 | Helson et al. |
| 2011/0287085 A1 | 11/2011 | Kurzrock et al. |
| 2012/0021036 A1 | 1/2012 | Majeti et al. |
| 2012/0031777 A1 | 2/2012 | Burke et al. |
| 2012/0040014 A1 | 2/2012 | Settineri et al. |
| 2012/0058208 A1 | 3/2012 | Jacob |
| 2012/0237590 A1 | 9/2012 | Helson |
| 2012/0308643 A1 | 12/2012 | Helson |
| 2013/0310351 A1 | 11/2013 | Milan et al. |
| 2013/0337488 A1 | 12/2013 | Helson |
| 2014/0050780 A1 | 2/2014 | Cerundolo et al. |
| 2015/0164878 A1 | 6/2015 | Helson |
| 2015/0343063 A1 | 12/2015 | Helson |
| 2016/0193149 A1 | 7/2016 | Helson |
| 2017/0095489 A1 | 4/2017 | Helson |
| 2017/0119802 A1 | 5/2017 | Helson |
| 2017/0246110 A1 | 8/2017 | Helson |
| 2017/0312366 A1 | 11/2017 | Helson |

FOREIGN PATENT DOCUMENTS

| | | |
|---|---|---|
| DE | 10029770 A1 | 12/2001 |
| EP | 3144006 | 9/2017 |
| JP | 10-279487 A | 10/1998 |
| JP | H10-191927 A | 7/2010 |
| WO | 2000070949 A1 | 11/2000 |
| WO | 2001093683 A1 | 12/2001 |
| WO | 2002002582 A1 | 1/2002 |
| WO | 2004047717 A2 | 6/2004 |
| WO | 2004080396 A2 | 9/2004 |
| WO | 2006061101 A2 | 6/2006 |
| WO | 2006131737 A2 | 12/2006 |
| WO | 2007062028 A2 | 5/2007 |
| WO | 2007103435 A2 | 9/2007 |
| WO | 2007129062 A1 | 11/2007 |
| WO | 2008045534 A2 | 4/2008 |
| WO | 2008063513 A2 | 5/2008 |
| WO | 2008128123 A2 | 10/2008 |
| WO | 2009051837 A2 | 4/2009 |
| WO | 2009073050 | 6/2009 |
| WO | 2010009186 A1 | 1/2010 |
| WO | 2010033692 A1 | 3/2010 |
| WO | 2010057332 A1 | 5/2010 |
| WO | 2011063178 A2 | 5/2011 |
| WO | 2011001351 A1 | 6/2011 |
| WO | 2011119588 A1 | 9/2011 |
| WO | 2012125830 A2 | 9/2012 |
| WO | 2012167212 A2 | 12/2012 |
| WO | 2013041894 | 3/2013 |
| WO | 2013166249 A1 | 11/2013 |
| WO | 2013188767 | 12/2013 |
| WO | 2013188767 A1 | 12/2013 |
| WO | 2015095576 A1 | 6/2015 |

OTHER PUBLICATIONS

Rodrigues et al (Derivative spectrophotometry as a tool for the determination of drug partition coefficients in water/dimyristoyl-L-alpha-phosphatidylglycerol (DMPG) liposomes. Biophys Chem. Dec. 11, 2001;94(1-2):97-106.*

Wong-Beringer et al (Lipid formulations of amphotericin B: clinical efficacy and toxicities. Clin Infect Dis. Sep. 1998;27(3):603-18).*

Tudaor et al (Amphotericin B® treatment causes QT prolongation in lung transplant-patients. Intensive Care Med Exp. Dec. 2015; 3(Suppl 1): A213).*

Rawal et al (Paclitaxel Induced Acute ST Elevation Myocardial Infarction: A Rare Case Report. Journal of Clinical and Diagnostic Research. Oct. 2016, vol. 10(10): XD01-XD02).*

Zhou, et al., "Correction of Defectrive Protein Trafficking of a Mutant HERG Potassium Channel in Human Long QT Syndrome," The Journal of Biological Chemistry, vol. 274:44, Oct. 29, 1999, pp. 31123-31126.

Pitman, Roger K., et al., "Conceptually Driven Pharmacologic Approaches to Acute Trauma," CNS Spectrums, Feb. 2005, vol. 10, No. 2, pp. 99-106.

Quan, Xiao-Qing, et al., "Increasing Gap Junction Coupling Reduces Transmural Dispersion of Repolarization and Prevents Torsade de Pointes in Rabbit LQT3 Model," J. Cardiovasc. Electrophysiol., vol. 18, Nov. 2007, pp. 1184-1189.

Rajamani, S., et al., "Drug-induced long QT syndrome: hERG K+ channel block and disruption of protein trafficking by fluoxetine and norfluoxetine," British Journal of Pharmacology, Sep. 11, 2006, vol. 149, pp. 481-489.

Rajeswari, A., et al., "Inhibition of monoamine oxidase-B by the polyphenolic compound, curcumin and its metabolite tetrahydrocurcumin, in a model of Parkinson's disease induced by MPTP neurodegeneration in mice," Inflammopharmacology, vol. 16, 2008, pp. 96-99.

Ranjan, A. P., et al, "Efficacy of Liposomal Curcumin in a Human Pancreatic Tumor Xenograft Model: Inhibition of Tumor Growth and Angiogenesis," Anticancer Research, vol. 33, Jul. 26, 2013, pp. 3603-3610.

Ravindran, J., et al., "Curcumin and Cancer Cells: How Many Ways Can Curry Kill Tumor Cells Selectively?," The AAPS Journal, vol. 11, No. 3, Jul. 10, 2009, pp. 495-510.

Roberts, A.N., et al., "Molecular and Functional Characterization of Amylin, a Peptide Associated with Type 2 Diabetes Mellitus," Proc. Natl. Acad. Sci. USA, Dec. 1989, vol. 86, pp. 9662-9666.

Rosi, S., et al., "Chemokine Receptor 5 Antagonist d-Ala-Peptide T-Amide Reduces Microglia and Astrocyte Activation Within the Hippocampus in a Neuroinflammatory Rat Model of Alzheimer's Disease," Neuroscience, (2005), vol. 134, pp. 671-676.

Rui, Pan, et al., "Curcumin Improves Learning and Memory Ability and its Neuroprotective Mechanism in Mice," Chin. Med. J., (2008), vol. 121, No. 9, pp. 832-839.

Rusinek, Henry, et al., "Hippocampal Blood Flow in Normal Aging Measured with Arterial Spin Lavelin at 3T," Magnetic Resonance in Medicine, (2011), 65:128-137.

Schena, Francesco P., et al., "Pathogenetic Mechanisms of Diabetic Nephropathy," J. Am. Soc. Nephrol., (2005), 16:S30-S33.

(56) References Cited

OTHER PUBLICATIONS

Segman, RH., et al., "Association Between the Dopamine Transporter Gene and Posttraumatic Stress Disorder," Molecular Psychiatry, (2002), vol. 7, pp. 903-907.
Segman, RH., et al., "Peripheral Blood Mononuclear Cell Gene Expression Profiles Identify Emergent Post-Traumatic Stress Disorder Among Trauma Survivors," Molecular Psychiatry, (2005), vol. 10, pp. 500-513.
Shah, et al., "Cardiovascular Safety of Tyrosine Kinase Inhibitors: With a Special Focus on Cardiac Repolarisation (QT Interval)," Drug Saf., Apr. 26, 2013, vol. 36, pp. 295-316.
Shaikh, J., et al, "Nanoparticle encapsulation improves oral bioavailability of curcumin by at least 9-fold when compared to curcumin administered with piperine as absorption enhancer," European Journal of Pharmaceutical Sciences, Elsevier, Amsterdam, NL, vol. 37, No. 3-4, Jun. 28, 2009, pp. 223-230.
Shimizu, Wataru, et al., "Sodium Channel Block with Mexiletine is Effective in Reducing Dispersion of Repolarization and Preventing Torsade de Pointes in LQT2 and LQT3 Models of the Long-QT Syndrome," vol. 96, Apr. 28, 1997, pp. 2038-2047.
Shimizu, Wataru, et al. "Effects of a K+ Channel Opener to Reduce Transmural Dispersion of Repolarization and Prevent Torsade de Pointes in LQT1, LQT2, and LQT3 Models of the Long-QT Syndrome," Circulation, 2000, 102:706-712.
Singh, Sonal, et al., "Long-Term Risk of Cardovascular Events with Rosiglitazone," JAMA, Sep. 12, 2007, vol. 298, No. 10, pp. 1189-1195.
Smith, Judith A., et al., "Abstract A29: Development of Liiposomal Curcumin as a New Potential Anticancer Agent," Molecular Cancer Therapeutics, Dec. 2009, vol. 8, Issue 12, Supplement 1, 1 page.
Stansfeld, Phillip, J., et al., "Drug Block of the hERG Potassium Channel: Insight From Modeling," Proteins: Structure, Function and Bioinformatics, Apr. 19, 2007, 68:568-580.
Stein, Murray B., et al., "Genetic and Environmental Influences on Trauma Exposure and Posttraumatic Stress Disorder Symptoms: A Twin Study," Am. J. Psychiatry, Oct. 2002, vol. 159, No. 10, pp. 1675-1681.
Sun, M., et al., "Enhancement of transport of curcumin to brain in mice by poly(n-butylcyanoacrylate) nanoparticle," J. Nanopart Res., vol. 12, 2010, pp. 3111-3122.
TASIGNA Package insert, Novartis Pharmaceuticals, Revised Sep. 2013.
Tonnesen, Hanne, H., et al, "Studies on curcumin and curcuminoids: XXV. Inhibition of primaquine-induced lysis of human red blood cells by curcumin," International Journal of Pharmaceutics 110 (1994) 161-167.
U.S. Department of Health and Human Services, "Guidance for Industry, S7B Nonclinical Evaluation of the Potential for Delayed Ventricular Repolarization (QT Interval Prolongation) by Human Pharmaceuticals," Oct. 2005, pp. 1-13.
Van De Water, et al., "An Improved Method to Correct the QT Interval of the Electrocardiogram for Changes in Heart Rate," Journal of Pharmacological Methods, Apr. 1989, vol. 22, pp. 207-217.
Verma, Richa, et al., "Structural and functional changes in a syntheitic S5 segment of KvLQT1 channel as a result of a conserved amino acid substitution that occurs in LQT1 syndrome of human," Biochimica et Biophysica Acta, 1798, Jan. 2010, pp. 461-470.
Vidal, Alessandra Teixeira, et al., "Prolonged cardioprotective effect of pyridostigmine encapsulated in liposomes," Life Sciences, vol. 86, 2010, pp. 17-23.
Wang, Timothy C., et al., "Pancreatic Gastrin Stimulates Islet Differentiation of Transforming Growth Factor a-Induced Ductular Precursor Cells," The Journal of Clinical Investigation, Inc., Sep. 1993, vol. 92, pp. 1349-1356.
Wang, Jingxiong, et al., "Phospholipid metabolite 1-palmitoyl-lysophosphatidylcholine enhances human ether-a-go-go-related gene (HERG) K+ channel function", Circulation, 2001, vol. 104, No. 22, pp. 2645-2648.

Wesley, Umadevi V., et al., "Role for Dipeptidyl Peptidase IV in Tumor Suppression of Human Non Small Cell Lung Carcinoma Cells," Int. J. Cancer, (2004), 109:855-866.
Wesley, Umadevi V., et al., "Dipeptidyl Peptidase Inhibits Maignant Phenotype of Prostate Cancer Cells by Blocking Basic Fibroblast Growth Factor Signaling Pathway," Cancer Res. (2005), a65:1325-1334.
Witchel, "Drug-induced hERG Block and Long QT Syndrome," Cardiovascular Therapeutics, 2011, vol. 29, pp. 251-259.
Wu, Aiguo, et al., "Brain and Spinal Cord Interaction: A Dietary Curcumin Derivative Counteracts Locomotor and Cognitive Deficits After Brain Trauma," Neurohabil Neural Repair, May 2011, 25(4):332-342.
Xalkori Package insert, Pfizer Laboratories, revised Feb. 2013, 10 pp.
Xu, Ying, et al., "Curcumin Reverses Impaired Hippocampal Neurogenesis and Increases Serotonin Receptor 1A mRNA and Brain-Derived Neurotrophic Factor Expression in Chronically Stressed Rats," Brain Research, (2007), 1162, pp. 9-18.
Yang, Ping, et al., "Allelic Variants in Long-QT Disease Genese in Patients with Drug Associated Rosades de Pointes," Circulation, Apr. 23, 2002, pp. 1943-1948.
Yap, Y. G., et al., "Drug Induced QT Prolongation and Torsades de Pointes," Heart, vol. 89, Nov. 2003, pp. 1363-1372.
Zachariae, U., et al., "Side chain flexabilities in the human ether-a-go-go related potassium channel (hERG) together with matched-pair binding studies suggest a new binding mode for channel blockers," J. Med. Chem., vol. 52 (14),Jan. 2, 2009, pp. 4266-4276.
Zhang, L., et al., "Self-Assembled Lipid—Polymer Hybrid Nanoparticles: A Robust Drug Delivery Platform," ACS Nano, vol. 2:8, Jul. 23, 2008, pp. 1696-1702.
Zhou, L., et al., "Nilotinib for Imatinib-Resistant or -Intolerant Chronic Myeloid Leukemia in Chronic Phase, Accelerated Phase, or Blast Crisis: A Single- and Multiple-Dose, Open-Label Pharmacokinetic Study in Chinese Patients," Clinical Therapeutics, vol. 31:7, Jul. 2009, pp. 1568-1575.
Extended European Search Report and Europeean Search Opinion for EPO 10832224.9 dated Feb. 26, 2013, 5 pages.
Extended and Supplemental European Search Report for EPO 11760055.1 dated Jun. 13, 2014, 7 pages.
Extended European Search Report and Europeean Search Opinion for EPO 12757689.0 dated Oct. 22, 2014, 7 pages.
Extended European Search Report and European Search Opinion for 12792560.0 dated Oct. 30, 2014, 11 pages.
International Search Report and Written Opinion for PCT/US2010/057332, dated Aug. 2, 2011, 12 pages.
International Search Report and Written Opinion for PCT/US2011/029393, dated Jun. 23, 2011, 17 pages.
International Search Report and Written Opinion for PCT/US2012/029230, dated Sep. 21, 2012, 14 pages.
International Search Report and Written Opinion for PCT/US2012/040637, dated Dec. 12, 2012, 13 pages.
International Search Report and Written Opinion for PCT/US2014/071246, dated Mar. 27, 2015, 14 pages.
International Search Report and Written Opinion for PCT/US2015/034078, dated Aug. 31, 2015, 17 pages.
International Search Report and Written Opinion for PCT/US2013/057744 dated Dec. 12, 2013, 14 pages.
Abel, Ted., et al., "Epigenetic Targets of HDAC Inhibition in Neurodegenerative and Psychiatric Disorders," Current Opinion in Pharmacology, (2008), vol. 8, pp. 57-64.
Aggarwal, et al., "The Molecular Targets and Therapeutic Uses of Curcumin in Health and Disease," (2006), Springer, 515 pages.
Anderson, P., et al., "The Hippocampus Book," Oxfored University Press, 2006, 102 pages.
Anderson, Corey, et al., "Most LQT2 Mutations Reduce Kv11.1 (hERG) Current by a Class 2 (Trafficking-Deficient) Mechanism," Circuilation, Nov. 11, 2005, pp. 365-373.
Arbiser, Jack L., et al., "Curcumin is an In Vivo Inhibitor of Angiogenesis," Moledular Medicine, (1998), 4:376-383.

(56) References Cited

OTHER PUBLICATIONS

Ataie, Amin, et al., "Neuroprotective Effects of the Polyphenolic Antioxidant Agnet, Curcumin, Against Homocysteine-Induced Cognitive Impairment and Oxidative Stress in the Rat," Pharmacology, Biochemistry and Behavior, (2010), vol. 96, pp. 378-385.
Bala, Kiran, et al., "Neuroprotective and Anti-Aging Effects of Curcumin in Aged Rat Brain Regions," Biogerontology, (2006), vol. 7, pp. 81-89.
Begum, A.N., et al., "Curcumin Structure-Function, Bioavailibility, and Efficacy in Models of Neuroinflammation and Alzheimer's Disease," The Journal of Pharmacoloby and Experimental Therapeutics, vol. 326:1, Apr. 15, 2008, pp. 196-208.
Bentzen, Peter J., et al., "Curcumin Induced Suicidal Erythrocyte Death," Cellular Physiology and Biochemistry, (2007), 19:153-164.
Bisht, Savita, et al., "Polymeric Nanoparticle-Encapsulated Curcumin ("Nanocurcumin"): A Novel Strategy for Human Cancer Therapy," Journal of Nanobiotechnology, (2007), 18 pages.
Bisht, Savita, et al., "Systemic Administration of Polymeric Nanoparticle-Encapsulated Curcumin (NanoCurcTM) Blocks Tumor Growth and Metastases in Preclinical Models of Pancreatic Cancer," Mol. Cancer Ther., (Aug. 2010), 9(8)2255-2264.
Blomgren, Kerstin, et al., "Obesity and Treatment of Diabetes with Glyburide may Both be Risk Factors for Acute Pancreatitis," Diabetes Care, (2002), 25:298-302.
Brownlee, Michael, "Biochemistry and Molecular Cell Biology of Diabetic Complications," Nature, Dec. 13, 2001, vol. 414, pp. 813-820.
Chao, Chun C., et al., "Glia: The Not So Innocent Bystanders," Journal of NeuroVirology, (1996), 2:234-239.
Chen, Shali, et al., "High glucose-induced, endothelin-dependent fibronectin synthesis is mediated via NF-kB and AP-1," Am J. Physiol. Cell Physiol., Sep. 18, 2002, 284:C263-C272.
Chen, et al., "An in vitro study of liposomal curcumin: stability, toxicity and biological activity in human lymphocytes and epstein-barr virus-transformed human B-cells," International Journal of Pharmaceutics, Jan. 2009, vol. 366, Issue 1-2, pp. 133-139.
Chiu, Jane, et al., "Curcumin Prevents Diabetes-Associated Abnormalities in the Kidneys by Inhibiting p300 and Nuclear Factor-kB," Nutrition, (2009), 25:964-972.
Compton, SJ, et al., "Genetically Defined Therapy of Inherited Long-QT Syndrome. Correction of Abnormal Repolarization by Potassium," Circulation, 1996; 94:1018-1022.
Crack, Peter J., et al., "Glutathione Peroxidase-1 Contributes to the Neuroprotection Seen in the Superoxide Dismutase-1 Transgenic Mouse in Response to Ischemia/Reperfusion Injury," Journal of Cerebral Blood Flow and Metabolism, (2003), vol. 23, No. 1, pp. 19-22.
Crouch, et al., "Clinical Relevance and Management of Drug-Related QT Interval Prolongation," Pharmacotherapy, Nov. 7, 2003, vol. 23:7, pp. 881-908.
D'Amico, Michele, et al., "Long-Term Inhibition of Dipeptidyl Peptidase-4 in Alzheimer's Prone Mice," Experimental Gerontology 45,3, (2010), 24 pages.
Djeddi, D, et al., "A: Effect of Domperidone on QT Interval in Neonates," J Pediatrics, 2008; 153(5):596-598.
Doherty, K., et al., "Multi-parameter in vitro toxicity testing of crizotinib, sunitinib, erlotinib, and nilotinib in human cardiomyocytes," Toxicoloty and Applied Pharmacology, Apr. 28, 2003, vol. 272, pp. 245-255.
Ducroq, J, et al., "Printemps R, Le Grand M.: Additive Effects Ziprasidone and D,L-Sotalol on the Action Potential in Rabbit Purkinje Fibers and on the hERG Potassium Current," J.Pharmacol. Toxicol Methods, 2005; 52:115-122.
Chartrand, et al., "Potential role of the membrane in hERG channel functioning and drug-induced long QT syndrome," Biochimica et Biophysica Acta, May 25, 2010, vol. 1798, pp. 1651-1662.
Chayanupatkul, "Cirrhotic cardiomyopathy: review of pathophysiology and treatment." Hepatol Int., Jul. 2014, vol. B, No. 3, pp. 308-315.

Dhandapani, K. M., et al., "Curcumin suppresses growth and chemoresistance of human glioblastoma cells via AP-1 and NFkB transcription factors," J. Neurochem (2007) 102:522-538.
Dhule, S.S., et al., "The Combined Effect of Encapsulating Curcumin and C6 Ceramide in Liposomal Nanoparticles against Osteosarcoma," Molecular Pharmaceutics, vol. 11, No. 2, Dec. 31, 2013, pp. 417-427.
Extended European Search Report and European Search Opinion for 14864686.2 dated May 4, 2017, 8 pages.
Extended European Search Report and European Search Opinion for 16188460.6 dated Nov. 16, 2016, 12 pages.
Gilenya (Fingolimod) Full Prescribing Information, Novartis: T2016-22, Feb. 2016, 25 pp.
Gou, M., et al., "Curcumin-loaded biodegradable polymeric micelles for colon cancer therapy in vitro and in vivo," Nanoscale, vol. 3, No. 4, Oct. 2010, pp. 1558-1567.
International Search Report and Written Opinion for PCT/US2013/045898, dated Sep. 6, 2013, 12 pages.
Leung, et al., "Effective stablization of curcumin by association to plasma proteins: human serum albumin and fibronogen," Langmuir, Mar. 25, 2009, vol. 25, Issue 10, pp. 5773-5777.
National Biodiversity Authority, Secretary of Government of India, Third Party Observation for Application No. EP20110760055, submitted for observation on Jul. 20, 2017, 7 pp.
Pisarik, et al., "Reduction of free amphothericin B Acute Toxicity in Mice after intravenous administration of empty liposomes," Journal of Infectious Diseases, May 1990, 161(5), pp. 1042-1044.
Ramachandran, C., et al., "Potentiation of Etoposide and Temozolomide Cytotoxicity by Curcumin and Turmeric Force in Brain Tumer Cell Lines," Journal of Complementary and Integrative Medicine (2012), 9(1):Article 20.
Ranjan, A.P., et al., "Efficacy of Liposomal Curcumin in a Human Pancreatic Tumor Xenograft Model: Inhibition of Tumor Growth and Angiogensis," Anticancer Research, vol. 33, No. 9, Jul. 26, 2013, pp. 3603-3609.
Ravindran, J., et al., "Curcumin and Cancer Cells: How Many Ways Can Currly Kill Tumor Cells Selectively?," The AAPS Journal, vol. 11:3, Sep. 2009, pp. 495-510.
Tang, H., et al., "Curcumin Polymers as Anticancer Conjugates," Biomaterials, vol. 31, No. 27, Jun. 29, 2010, pp. 7139-7149.
Vincenzi, Frank F., et al., "Citalopram-Induced Long QT Syndrome and the Mammalian Dive Reflex," Drug Saf-Case Rep, vol. 2:12, Aug. 1, 2015, 5 pp.
WHO Model List of Essential Medicines, World Health Organization, Oct. 2013. pp. 1-47.
Yagi, Y., et al., "Analysis of Onset Mechanisms of a Sphingosine 1-Phosphate Receptor Modulator Fingolimod-Induced Atrioventricular Conduction Block and QT-Interval Prolongation," Toxicology and Applied Pharmacology, Sep. 16, 2014, 281, pp. 39-47.
Zeltser, et al., "Drug-induced atrioventricular block: prognosis after discontinuation of the culprit drug." Journal of the American College of Cardiology, Jul. 2004, vol. 44, No. 1, pp. 105-108.
International Search Report and Written Opinion for PCT/US2017/057446, dated Dec. 29, 2017, 13 pp.
Rawal, et al., "Paclitaxel Induced Acute ST Elevation Myocardial Infarction: A Rare Case Report," Journal of Clinical and Diagnostic Research, Oct. 2016, vol. 10(10), pp. XD01-XD02.
Shopp, G.M., et al., "Liposomes ameliorate Crizotinib- and Nilotinib-induced inhibition of the cardiac IKr channel and Qtc prolongation," Anticancer Research, 2014, vol. 34, pp. 4733-4740.
Chinthalapally, et al., "Inhibition by dietary curcumin of azoxymethane-induced ornithine decarboxylase, tyrosine protein kinase, arachidonic acid metabolism and aberrant crypt foci formation in the rat colon," Carcinogensis, vol. 14, Iss. 11, Nov. 1, 1993, pp. 2219-2225.
Hasima, N., et al., "Cancer-linked targets modulated by curcumin," Int. J. Biochem. Mol. Bio., Dec. 30, 2012, vol. 3(4), pp. 328-351.
Hong, et al., "Curcumin inhibits tyrosine kinase activity of p195neu an also depletes p185neu," Clinical Cancer Research, Mar. 22, 1999, 5(7), pp. 1884-1891.
Reddy, S., et al, Curcumin is a non-competitive and selective inhibitor of phsophorylase kinase, FEBS Letters, Jan. 1994, 341, pp. 19-22.

(56) References Cited

OTHER PUBLICATIONS

Webster, G., et al., "Contemporary reviews in cardiovascular medicine, An Update on Channelopathies," Jan. 2013, vol. 127, pp. 126-140.
WIKIPEDIA2, https://en.wikipedia.org/wiki/Atrioventricular_block (downloaded on Jul. 26, 2018).
International Search Report and Written Opinion of Korean Intellectual Property Office for PCT/US2017/060936 dated Feb. 20, 2018, 13 pp.
Etheridge, SP, et al., "A New Oral Therapy for Long QT Syndrome: Long Term Oral Potassium Improves Repolarization in Patients with hERG Mutations," J AM Coll Cardiol, 2003; 42:1777-1782.
Everett, Peter C., et al., "Preclinical Assessment of Curcumin as a Potential Therapy for B-CLL," American Journal of Hematology, (2006), 8 pages.
Fahn, Stanlex, "Medical Treatment of Parkinson's Disease," Journal of Neurology, 1998, 245 (Supplement 3): P15-P24.
Fauchier, L, et al.,"JP: Effect of Verapamil on QT Interval Dynamicity," AM J Cardiol., 1999; 83(5):807-808 A10-1.
FDA Pharmacology Review of Xalkori (crizotinib), IND No. 202570, 2011a, www.accessdata.fda.gov/drugsatfda_docs/nda/2011/202570Orig1s000PharmR.pdf (accessed Oct. 9, 2013).
FDA Pharmacology of Tasigna® (nilotinib), IND No. 22-068, 2007a, www.accessdata.fda.gov/drugsatfda_docs/nda/2007/022068s000_PharmR_P1.pdf and www.accessdata.fda.gov/drugsatfda_docs/nda/2007/022068s000_MedR_P2.pdf, (accessed Oct. 25, 2013).
Fowler, NO, et al., "Electrocardiographic Changes and Cardiac Arrhythmias in Patients Receiving Psychotropic Drugs," Am J Cardiol, 1976; 37(2):223-230.
Garcia-Alloza, M., et al., "Curcumin Labels Amyloid Pathology in Vivo, Disrupts Existing Plaques, and Partially Restroes distorterneurites in an Alzheimer Mouse Model," Journal of Neurochemistry, (2007), vol. 102, pp. 1095-1104.
Grama, C.N., et al., "Poly(lactide—glycolide) nanoparticles for peroral delivery of bioactives," Current Opinion in Colloid and Interface Science, London, GB, vol. 16, No. 3, Nov. 24, 2010, pp. 238-245.
Gukovsky, Ilya, et al., "Curcumin Ameliorates Ethanol and Nonethanol Experimental Pancreatitis," Am. J. Physiol. Gastrointest. Liver Physiol., (2003), 284:G85-G95.
Harish, G., et al., "Bioconjugates of curcumin display improved protection against glutathione depletion mediated oxidative stress in a dopaminergic neuronal cell line: Implications for Parkinson's disease," Bioorgaic & Medicinal Chemistry, vol. 18, Feb. 20, 2010, pp. 2631-2638.
Helson, et al., "Liposome mitigation of curcumin inhibition of cardiac potassium delayed-rectifier current," Journal of Receptor, Ligand and Channel Research, Nov. 15, 2012, vol. 5, pp. 108.
Hernandez-Fonseca, Juan P., et al., "Structural and Ultrastructural Analysis of Cerebral Cortex, Cerebellum, and Hypothalamus from Diabetic Rats," Experimental Diabetes Research Oct. 1, 2009: 2009: 329632.
Jacob, Asha, et al., "Mechanism of the Anti-Inflammatory Effect of Curcumin: PPAR-γ Activation," Hindawi Publishing Corporation, PPAR Research, (2007), Article ID 89369, 5 pages.
Jervell, A, et al., "Congenital Deaf-Mutism, Functional Heart Disease with Prolongation of the QT Interval and Sudden Death," Am Heart J., 1957; 54(1):59-68.
Kang, J, et al., "Discovery of a Small Molecule Activator of the Human Ether-a-go-go -Related Gene(HERG) Cardiac K+ Channel," Mol Pharmacol, 2005(3); 67:827-836.
Katchman, AN, et al., "Comparative Evaluation of HERG Currents and QT Intervals Following Challenge with Suspected Torsadogenic and Nontorsdogenic Drugs," J Pharmacol Exp Ther., 2006; 316(3):1098-1106.
Kim, K-P., et al., "Nilotinib in Patients with GIST who failed imatinib and sunitinib: importance of prior surgery on drug bioavailability," Jul. 12, 2010, Cancer Chemother. Pharmacol., vol. 68, pp. 285-291.

Kim, So Jung, et al., "Curumin Stimulates Proliferation of Embryonic Neural Progenitor Cells and Neurogenesis in the Adult Hippocampus," The Journal of Biological Chemistry, May 23, 2008, vol. 283, No. 21, pp. 14497-14505.
Koehler, Jacqueline A., et al., "Glucagon-Like Peptide-1 Receptor Activation Modulates Pancreatitis-Associated Gene Expression Bud Does Not Modify the Susceptibility to Experimental Pancreatitis in Mice," Diabetes, Sep. 2009, vol. 58, pp. 2148-2161.
Konwarh, R., et al., "Poly(ethylene glycol)-magnetic nanoparticles-curcumin trio: Directed morphogenesis and synergistic free-radical scavenging," Colloids and Surfaces B: Biointerfaces, vol. 81, Aug. 7, 2010, pp. 578-586.
Kourelis, Taxiarchis V., et al., "Metformin and Cancer: New Applications for an Old Drug," Med. Oncol., Feb. 8, 2011, 14 pages.
Kowluru, Renu A., et al., "Effects of Curcumin on Retinal Oxidative Stress and Inflammation in Diabetes," Nutrition & Metabolism, Apr. 16, 2007, 8 pages.
Kulkarni, S.K., et al., "An Overview of Curcumin in Neurological Disorders," Indian J. Pharm. Sci, Jul. 1, 2010, 72:2, pp. 149-154.
Kumar, T. Peeyush, et al., "Curcumin Modulates Dopaminergic Receptor, CREB and Phospholipase C Gene Expression in the Cerebral Cortex and Cerebellum of Streptozotocin Induced Diabetic Rats," Journal of Biomedical Science, (2010), 2:43, 11 pages.
Lamont, Benjamin J., et al., "Differential Antidiabetic Efficacy of Incretin Agonists Versus DPP-4 Inhibition in High Fat-Fed Mice," Diabetes, Jan. 2008, vol. 57, pp. 190-198.
Layton, D, et al., "Prolongation of the QT interval and cardiac arrhythmias associated with cisapride: limitations of the pharmacoepidemiological studies conducted and proposals for the future," Pharmacoepidemiol Drug Saf., 12(1), Nov. 13, 2002, pp. 31-40.
Lee, et al., "Electrophysiological Effects of the Anti-Cancer Drug Lapatinib on Cardiac Repolarization," Basic & Clinical Pharmocology & Toxicology, vol. 107, Dec. 21, 2009, pp. 614-618.
Leung, et al., "Effective stabilization of curcumin by association to plasma proteins: human serum albumin and fibronogen," Langmuir, 2009, vol. 25, Issue 10, pp. 5773-5777.
Li, Yu-Cheng, et al., "Antidepressant-Like Effects of Curcumin on Serotonergic Receptor-Coupled Ac-cAMP Pathway in Chronic Unpredictable Mid Stress of Rats," Progress in Neuro-Psychophamacoloby & Biological Psychiatry, (2009), vol. 33, pp. 435-449.
Li, Lan, et al., "Liposome-Encapsulated Curcumin In Vitro and In Vivo Effects on Proliferation, Apoptosis, Signaling, and Angiogenesis," Cancer, May 4, 2005, 104:1322-1331.
Lim, Kah Jing, et al., "A Polymeric Nanoparticle Formulation of Curcumin Inhibits Growth, Clonogenicity and Stem-Like Fraction in Malignant Brain Tumors," Cancer Biology & Therapy, Mar. 1, 2011, 11:5, pp. 464-473.
Logan-Smith, Melanie J., et al., "Curcumin, a Molecule that Inhibits the Ca2+ -ATPase of Sarcoplasmic Reticulum but Increases the Rate of Accumulation of Ca2+," The Journal of Biological Chemistry, (2001), vol. 276, No. 50, pp. 46905-46911.
Mach, Claire M., et al., "Determination of Minimum Effective Dose and Optimal Dosing Schedule for Liposomal Curcumin in a Xenograft Human Pancreatic Cancer Model," (2009), Anticancer Research, 29:1895-1900.
Maciel, NR, et al., "Reduced Cardiovascular Alterations of Tarter Emetic Administered in Long-Circulating Liposomes in Rats," Toxicology Letters, 2010; 199(3):234-238.
Marino, Silvia, et al., "Sertaline in the Treatment of Depressive Disorders in Patients with Parkinson's Disease," Neurological Sciences, Nov. 2008, 29:391-395.
Matsushita, Yuichi, et al., "Activation of Peroxisome Proliferator-Activated Receptor d Inhibits Streptozotocin-Induced Diabetic Nephropathy Through Anti-Inflammatory Mechanisms in Mice," Diabetes, Mar. 2011, vol. 60, pp. 960-968.
Mayer, Lawrence D., et al., "Intravenous Pretreatment with Empty pH Liposomes Alters the Pharmacokinetics and Toxicity of Doxorubicin through In Vivo Active Drug Encapsulation," Journal of Pharmaceutical Sciences, vol. 88, No. 1, Nov. 25, 1998, pp. 96-102.

(56) References Cited

OTHER PUBLICATIONS

Mehta, RT, et al., "Formulation, toxicity, and antifungal activity in vitro of liposomal-encapsulated nystatin as therapeutic agent for systemic candidiasis," Antimicrob Agents Chemother., 31(12), Dec. 1987, pp. 1897-1900.

Mishra, S., et al., "The effect of curcumin (turmeric) on Alzheimer's disease: An overview," Annals of Indian Academy of Neurology, vol. 11:1, 2008, pp. 13-19.

Moha, H, et al., "Curcumin blocks the recombinant human cardiac KCNQ 1/KCNE 1 channels (IKs) stably expressed in HEK 293 cells," Abstract of 12th Annual Meeting of the French Society of Pharmacology and Therapeutics, Fund. & Clin. Pharma., vol. 22:1, Jun. 2008.

Mosse, et al., "Safety and activity of crizotinib for pediatric patients with refractory solid tumours of anaplastic large-cell lymphoma: a Children's Oncology Group phase 1 consortium study," Lancet Oncol., May 2013, vol. 14(6), pp. 472-480.

Mukerjee, Anindita, et al., "Formulation, Characterization and Evaluation of Curcumin-Loaded PLGA Nanospheres for Cancer Therapy," (2009), Anticancer Research 29:3867-3876.

Murphy, Eric, A., et al., "Targeted Nanogels: A Versatile Platform for Drug Delivery to Tumors," Molecular Cancer Therapeutics, Apr. 25, 2011; 10:972-982.

Nam, et al., "Curcumin-Loaded PLGA Nanoparticles Coating onto Metal Stent by Electrophoretic Deposition Techniques," Bull. Korean Chem. Soc., Jan. 2007, vol. 28, No. 3, pp. 397-402.

Narala, Venkata R., et al., "Curcumin is not a Ligand for Peroxisome Proliferator-Activated Receptor-Y," Gene Therm. Mol. Biol., Apr. 1, 2009, 13(1):20-25.

Naseem, et al., "Bupivacaine Extended Release Lipsome Injection Does not Prolong Qtc Interval in a Thorough QT/QTc Study in Healthy Volunteers," Journal of Clin. Pharma., 2012, vol. 52, pp. 1441-1447.

Nousiainen, T., et al., "QT dispersion and late potentials during doxorubicin therapy for non-Hodgkin's lymphoma," Journal of Internal Medicine, 245, 1999, pp. 359-364.

Olansky, Leann, "Do Incretin-Based Therapies Cause Acute Pancreatitis?" Journal of Diabetes Science and Technology, Jan. 2010, vol. 4, Issue 1, pp. 228-229.

\* cited by examiner

PROTECTIVE EFFECT OF DMPC, DMPG, DMPC/DMPG, LYSOPG AND LYSOPC AGAINST DRUGS THAT CAUSE CHANNELOPATHIES

CROSS-REFERENCE TO RELATED APPLICATIONS

This application is a continuation-in-part patent application of U.S. patent application Ser. No. 14/729,940 filed on Jun. 3, 2015, which claims priority to U.S. Provisional Application Ser. No. 62/007,244 filed on Jun. 3, 2014; this application is also a continuation-in-part patent application of U.S. patent application Ser. No. 14/575,644 filed on Dec. 18, 2014, which claims priority to U.S. Provisional Application Ser. No. 61/917,426 filed on Dec. 18, 2013; this application is also a continuation-in-part application of U.S. patent application Ser. No. 15/068,300 filed on Mar. 11, 2016, which is a continuation application that claims priority to U.S. patent application Ser. No. 14/268,376 filed on May 2, 2014, which is a continuation application that claims priority to U.S. patent application Ser. No. 13/487,233 filed on Jun. 3, 2012, now U.S. Pat. No. 8,753,674 issued on Jun. 17, 2014, which claims priority to U.S. Provisional Application Ser. No. 61/493,257 filed on Jun. 3, 2011, the entire contents of each, which are incorporated herein by reference.

STATEMENT OF FEDERALLY FUNDED RESEARCH

None.

INCORPORATION-BY-REFERENCE OF MATERIALS FILED ON COMPACT DISC

None.

TECHNICAL FIELD OF THE INVENTION

The present invention relates in general to the field of drug treatment, and more particularly, to novel compositions and methods for reducing or eliminating channelopathies or conditions resulting from irregularities or alterations in cardiac patterns caused by an active agent or a drug.

BACKGROUND OF THE INVENTION

Without limiting the scope of the invention, its background is described in connection with compositions and methods for controlling the duration of repolarization of the cardiac ventricle QT in a subject comprising administering to subject in need thereof of a modification of or functional interference with a therapeutic agent, or congenital defect which if unmodified can induce prolongation of repolarization in the heart myocyte action potential, torsade de points, and the long QT syndrome.

The beating of the heart is due to precisely controlled regularly spaced waves of myocardial excitation and contraction. The electrical currents during ion-based depolarization and repolarization can be measured by electrical leads placed on the body in specific locations (the electrocardiogram) which measure electrical waves. The P-wave represents a wave of depolarization in the atrium. When the entire atria becomes depolarized, the wave returns to zero. After 0.1 seconds the ventricle is entirely depolarized resulting in the QRS complex. The three peaks are due to the way the current spreads in the ventricles. This is followed by the T-wave or repolarization of the ventricle. The QT interval measured from the beginning of the QRS complex to the end of the T wave on the standard ECG represents the duration till the completion of the repolarization phase of the cardiac myocyte (or the depolarization and repolarization of the ventricle). The duration of this interval can vary due to genetic variation, cardiac disease, electrolyte balance, envenomation, and drugs. Prolongation of the QT interval can result in ventricular arrhythmias and sudden death.

Drug induced long QTc Syndrome (LQTS) i.e., a prolongation of the action potential duration is a common cause of governmental mandated drug withdrawal. QTc prolongation is an unpredictable risk factor for Torsades de Pointes (TdP), a polymorphic ventricular tachycardia leading to ventricular fibrillation. Drug induced LQTS comprises about 3% of all prescriptions which when followed by TdP may constitute a lethal adverse reaction. Patients taking one or more than one QTc-prolonging drug concomitantly, have an enhanced risk of TdP. While the overall occurrence of TdP is statistically rare but clinically significant for the affected individual, assay for this drug effect is a mandatory requirement prior to allowing a drug to enter clinical trials.

Common structurally diverse drugs block the human ether-a-go-go-related gene (KCNH2 or hERG) coded $K^+$ channel and the cardiac delayed-rectifier potassium current $I_K$ (KV11.1) resulting in acquired LQTS. Drug-associated increased risk of LQTS is a major drug development hurdle and many drugs have been withdrawn during pre-clinical development, or assigned black box warnings following approval or withdrawn from the market. Autosomal recessive or dominant LQTS based upon 500 possible mutations in 10 different genes coding for the potassium channel has an incidence of 1:3000 or about 100,000 persons in the US. Prolonged QT intervals, or risk of LQTS occur in 2.5% of the asymptomatic US population. This syndrome when expressed can lead to severe cardiac arrhythmia and sudden death in untreated patients. The probability of cardiac death in patients with asymptomatic congenital LQTS who are medicated with LQTS-inducing drugs is increased.

The majority of the acquired LTQS drug withdrawals are due to obstruction of the potassium ion channels coded by the human ether-a-go-go related gene (hERG). High concentrations of hERG blocking drugs generally induce a prolonged QTc interval and increase the probability of TdP. Up to 10% of cases of drug-induced TdP can be due to due to 13 major genetic mutations, 471 different mutations, and 124 polymorphisms (Chig, C 2006).

Systems and methods for detection of LQTS have been described previously. For example U.S. Patent Publication No. 2010/0004549 (Kohls et al. 2010) discloses a system and method of detecting LQTS in a patient by comparing a collected set of ECG data from the patient to a plurality of databases of collected ECG data. The plurality of databases will include a database containing previous ECGs from the patient, a known acquired LQTS characteristics database, and a known genetic LQTS characteristics database. Comparing the patient's ECG to these databases will facilitate the detection of such occurrences as changes in QT interval from success of ECGs, changes in T-wave morphology, changes in U-wave morphology, and can match known genetic patterns of LQTS. The system and method is sensitive to patient gender and ethnicity, as these factors have been shown to effect LQTS, and is furthermore capable of matching a QT duration to a database of drug effects. The system and method is also easily integrated into current ECG management systems and storage devices.

A system and method for the diagnosis and treatment of LQTS is described in U.S. Patent Publication No. 2008/0255464 (Michael, 2008). The Michael invention includes a system for diagnosing Long QT Syndrome (LQTS) derives a QT/QS2 ratio from an electrical systole (QT) and a mechanical systole (QS2) to detect a prolonged QT interval in a patient's cardiac cycle. A processor acquires the systoles from a microphone and chest electrodes, calculates the QT/QS2 ratio, and outputs the result to a display. The processor may compare the QT/QS2 ratio to a threshold value stored in memory for diagnosing LQTS in the patient. A user interface provides for programming, set-up, and customizing the display. A mode selector allows the system to operate alternatively as a phonocardiograph, a 12 lead electrocardiograph, or a machine for diagnosing LQTS. A related method for diagnosing cardiac disorders such as LQTS includes measuring QT and QS2 during a same cardiac cycle, calculating a QT/QS2 ratio, and comparing the result to a threshold value derived from empirical data. The method may include measuring systoles both at rest and during exercise, and may be used for drug efficacy, dosage optimization, and acquired LQTS causality tests.

A method for the treatment of cardiac arrhythmias is provided in U.S. Patent Publication No. 2007/0048284 (Donahue and Marban, 2007). The method includes administering an amount of at least one polynucleotide that modulates an electrical property of the heart. The polynucleotides of the invention may also be used with a microdelivery vehicle such as cationic liposomes and adenoviral vectors.

Methods, compositions, dosing regimes, and routes of administration for the treatment or prevention of arrhythmias have been described by Fedida et al. (2010) in U.S. Patent Publication No. 2001/00120890. In the Fedida invention, early after depolarizations and prolongation of QT interval may be reduced or eliminated by administering ion channel modulating compounds to a subject in need thereof. The ion channel modulating compounds may be cycloalkylamine ether compounds, particularly cyclohexylamine ether compounds. Also described are compositions of ion channel modulating compounds and drugs which induce early after depolarizations, prolongation of QT interval and/or Torsades de Pointes. The Fedida invention also discloses antioxidants which may be provided in combination with the ion channel modulating compounds, non-limiting examples of the antioxidants include vitamin C, vitamin E, beta-carotene, lutein, lycopene, vitamin B2, coenzyme Q10, cysteine as well as herbs, such as bilberry, turmeric (curcumin), grape seed or pine bark extracts, and ginkgo.

SUMMARY OF THE INVENTION

In one embodiment, the present invention includes a composition for preventing one or more cardiac channelopathies or conditions resulting from irregularities or alterations in cardiac patterns caused by an active agent or a drug in a human or animal subject comprising: an amount of a lysophosphatidylglycerol adapted for oral administration effective to reduce or prevent one or more cardiac channelopathies or conditions resulting from irregularities or alterations in cardiac patterns caused by the active agent or drug. In one aspect, the lysophosphatidylglycerol includes at least one of a lysophosphatidylcholine, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine or erucoyl-lysophosphatidylcholine. In another aspect, the lysophosphatidylglycerol include at least one or 1-Myristoyl-2-Hydroxy-sn-Glycero-3-Phosphocholine (DMPC), 12-Mysteroyl-2-Hydroxy-sn-Glycero-3-[Phospho-rac-(glycerol)](DMPG), DMPC/DMPG, 1-myristoyl-2-hydroxy-sn-glycero-3-phospho-(1'-rac-glycerol) (LysoPG), or 1-myristoyl-2-hydroxy-sn-glycero-3-phosphocholine (LysoPC). In another aspect, the lysophosphatidylglycerol is defined further as a short chain fatty acid is up to 5 carbons, a medium chain is 6 to 12 carbons, a long chain is 13-21 carbons and a very long chain fatty acid is greater than 22 carbons, including both even and odd chain fatty acids. In another aspect, the lysophosphatidylglycerol has 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55 or more carbons, which are saturated or unsaturated. In another aspect, the cardiac channelopathy or the condition resulting from the irregularity or alteration in the cardiac pattern is inhibition of an ion channel responsible for the delayed-rectifier $K^+$ current in the heart, polymorphic ventricular tachycardia, prolongation of the QTc, LQT2, LQTS, or torsades de pointes. In another aspect, the composition is used for the treatment or prevention of prolongation of the $I_{Kr}$ channel inhibition or QT prolongation induced by administration of the active agent or drug used in the treatment of cardiac, allergic, or cancer related diseases. In another aspect, the active agent drug is selected from at least one of crizotinib, nilotinib, terfenadine, astemizole, gripafloxacin, terodilene, droperidole, lidoflazine, levomethadyl, sertindoyle or cisapride. In another aspect, the active agent drug is provided enterally, parenterally, intravenously, intraperitoneally, or orally. In another aspect, the active agent drug is provided in a liposomes and comprises a lipid or a phospholipid wall, wherein the lipids or the phospholipids are selected from the group consisting of phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, and diacylglycerolsuccinate. In another aspect, the drug is selected from Albuterol (salbutamol), Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Crizotinib, Dabrafenib, Dasatinib, Desipramine, Dexmedetomidine, Dexmethylphenidate, Dextroamphetamine (d-Amphetamine), Dihydroartemisinin+piperaquine, Diphenhydramine, Disopyramide, Dobutamine, Dofetilide, Dolasetron, Domperidone, Dopamine, Doxepin, Dronedarone, Droperidol, Ephedrine, Epinephrine (Adrenaline), Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide (Frusemide), Galantamine, Gatifloxacin, Gemifloxacin, Granisetron, Halofantrine, Haloperidol, Hydrochlorothiazide, Ibutilide, Iloperidone, Imipramine (melipramine), Indapamide, Isoproterenol, Isradipine, Itraconazole, Ivabradine, Ketoconazole, Lapatinib, Levalbuterol (levsalbutamol), Levofloxacin, Levomethadyl, Lisdexamfetamine, Lithium, Mesoridazine, Metaproterenol, Methadone, Methamphetamine (methamfetamine), Methylphenidate, Midodrine, Mifepristone, Mirabegron, Mirtazapine, Moexipril/HCTZ, Moxifloxacin, Nelfinavir, Nicardipine, Nilotinib, Norepinephrine (noradrenaline), Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone.

In one embodiment, the present invention includes a composition for preventing or treating diseases with an active agent or drug that causes one or more adverse reactions arising from administration of an active agent or drug in a human that causes at least one of cardiac channelopathies, $I_{Kr}$ channel inhibition or QT prolongation comprising:

an amount of a lysophosphatidylglycerol with a basic structure:

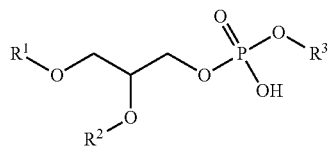

wherein $R^1$ or $R^2$ can be any even or odd-chain fatty acid, and $R^3$ can be H, acyl, alkyl, aryl, amino acid, alkenes, alkynes, adapted for oral administration effective to reduce or prevent the at least one cardiac channelopathies, $I_{Kr}$ channel inhibition or QT prolongation caused by the drug; and one or more active agents or drugs that cause at least one of $I_{Kr}$ channel inhibition or QT prolongation. In one aspect, the lysophosphatidylglycerol includes at least one of a lysophosphatidylcholine, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine or erucoyl-lysophosphatidylcholine. In another aspect, the liposome or liposome precursors are selected from at least one or 1-Myristoyl-2-Hydroxy-sn-Glycero-3-Phosphocholine (DMPC), 12-Mysteroyl-2-Hydroxy-sn-Glycero-3-[Phospho-rac-(glycerol)] (DMPG), DMPC/DMPG, 1-myristoyl-2-hydroxy-sn-glycero-3-phospho-(1'-rac-glycerol) (LysoPG), or 1-myristoyl-2-hydroxy-sn-glycero-3-phosphocholine (LysoPC). In another aspect, the short chain fatty acid is up to 5 carbons, a medium chain is 6 to 12 carbons, a long chain is 13-21 carbons and a very long chain fatty acid is greater than 22 carbons, including both even and odd chain fatty acids. In another aspect, the short chain fatty acid has 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55 or more carbons, which are saturated or unsaturated. In another aspect, the cardiac channelopathy or the condition resulting from the irregularity or alteration in the cardiac pattern is inhibition of an ion channel responsible for the delayed-rectifier $K^+$ current in the heart, polymorphic ventricular tachycardia, prolongation of the QTc, LQT2, LQTS, or torsades de pointes. In another aspect, the composition is used for the treatment or prevention of prolongation of the $I_{Kr}$ channel inhibition or QT prolongation induced by administration of one or more drugs used in the treatment of cardiac, allergic, or cancer related disease. In another aspect, the one or more active agents is selected from at least one of crizotinib, nilotinib, terfenadine, astemizole, gripafloxacin, terodilene, droperidole, lidoflazine, levomethadyl, sertindoyle or cisapride. In another aspect, the active agent or drug is provided enterally, parenterally, intravenously, intraperitoneally, or orally. In another aspect, the liposomes comprises a lipid or a phospholipid wall, wherein the lipids or the phospholipids are selected from the group consisting of phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, and diacylglycerolsuccinate. In another aspect, the drug is selected from Albuterol (salbutamol), Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Crizotinib, Dabrafenib, Dasatinib, Desipramine, Dexmedetomidine, Dexmethylphenidate, Dextroamphetamine (d-Amphetamine), Dihydroartemisinin+piperaquine, Diphenhydramine, Disopyramide, Dobutamine, Dofetilide, Dolasetron, Domperidone, Dopamine, Doxepin, Dronedarone, Droperidol, Ephedrine, Epinephrine (Adrenaline), Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide (Frusemide), Galantamine, Gatifloxacin, Gemifloxacin, Granisetron, Halofantrine, Haloperidol, Hydrochlorothiazide, Ibutilide, Iloperidone, Imipramine (melipramine), Indapamide, Isoproterenol, Isradipine, Itraconazole, Ivabradine, Ketoconazole, Lapatinib, Levalbuterol (levsalbutamol), Levofloxacin, Levomethadyl, Lisdexamfetamine, Lithium, Mesoridazine, Metaproterenol, Methadone, Methamphetamine (methamfetamine), Methylphenidate, Midodrine, Mifepristone, Mirabegron, Mirtazapine, Moexipril/HCTZ, Moxifloxacin, Nelfinavir, Nicardipine, Nilotinib, Norepinephrine (noradrenaline), Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone.

In one embodiment, the present invention includes a method for preventing or treating one or more cardiac channelopathies, irregularities or alterations in cardiac patterns, $I_{Kr}$ channel inhibition or QT prolongation, in a human or animal subject caused by an active agent or drug, wherein the active agents or drugs are used to treat a disease in a human or animal subject comprising the steps of: administering to the human or animal subject an amount of a lysophosphatidylglycerol adapted for oral administration effective to reduce or prevent one or cardiac channelopathies, irregularities or alterations in cardiac patterns, $I_{Kr}$ channel inhibition, or QT prolongation caused by the active agent or drug; and an effective amount of the active agent or drug sufficient to treat the disease, wherein the orally provided lysophosphatidylglycerol reduces or eliminates the at least one cardiac channelopathies, irregularities or alterations in cardiac patterns, $I_{Kr}$ channel inhibition or QT prolongation. In one aspect, the lysophosphatidylglycerol includes at least one of a lysophosphatidylcholine, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine or erucoyl-lysophosphatidylcholine. In another aspect, the liposome or liposome precursor are selected from at least one or 1-Myristoyl-2-Hydroxy-sn-Glycero-3-Phosphocholine (DMPC), 12-Mysteroyl-2-Hydroxy-sn-Glycero-3-[Phospho-rac-(glycerol)] (DMPG), DMPC/DMPG, 1-myristoyl-2-hydroxy-sn-glycero-3-phospho-(1'-rac-glycerol) (LysoPG), or 1-myristoyl-2-hydroxy-sn-glycero-3-phosphocholine (LysoPC). In another aspect, the short chain fatty acid is up to 5 carbons, a medium chain is 6 to 12 carbons, a long chain is 13-21 carbons and a very long chain fatty acid is greater than 22 carbons, including both even and odd chain fatty acids. In another aspect, the short chain fatty acid has 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55 or more carbons, which are saturated or unsaturated. In another aspect, the cardiac channelopathy or the condition resulting from the irregularity or alteration in the cardiac pattern is inhibition of an ion channel responsible for the delayed-rectifier $K^+$ current in the heart, polymorphic ventricular tachycardia, prolongation of the QTc, LQT2, LQTS, or torsades de pointes. In another aspect, the one or more active agents is selected from at least one of crizotinib, nilotinib, terfenadine, astemizole, gripafloxacin, terodilene, droperidole, lidoflazine, levomethadyl, sertindoyle or cisapride. In another aspect, the drug is selected from Albuterol (salbutamol), Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Crizotinib, Dabrafenib, Dasatinib, Desipramine, Dexmedetomidine, Dexmethylphenidate, Dextroamphetamine (d-Amphetamine), Dihydroartemisinin+piperaquine, Diphenhydramine, Disopyramide, Dobutamine, Dofetilide, Dolasetron, Domperidone, Dopamine, Doxepin, Dronedarone, Droperidol, Ephedrine, Epinephrine (Adrenaline), Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide (Frusemide), Galantamine, Gatifloxacin, Gemifloxacin, Granisetron, Halofantrine, Haloperidol, Hydrochlorothiazide, Ibutilide, Iloperidone, Imipramine (melipramine), Indapamide, Isoproterenol, Isradipine, Itraconazole, Ivabradine, Ketoconazole, Lapatinib, Levalbuterol (levsalbutamol), Levofloxacin, Levomethadyl, Lisdexamfetamine, Lithium, Mesoridazine, Metaproterenol, Methadone, Methamphetamine (methamfetamine), Methylphenidate, Midodrine, Mifepristone, Mirabegron, Mirtazapine, Moexipril/HCTZ, Moxifloxacin, Nelfinavir, Nicardipine, Nilotinib, Norepinephrine (noradrenaline), Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone.

In one embodiment, the present invention includes a method for preventing or treating one or more adverse reactions arising from administration of a therapeutically active agent or a drug in a human or animal subject comprising the steps of: administering to the human or animal subject an amount of an amount of a lysophosphatidylglycerol with a basic structure:

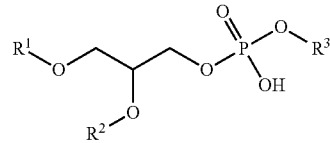

wherein $R^1$ or $R^2$ can be any even or odd-chain fatty acid, and $R^3$ can be H, acyl, alkyl, aryl, amino acid, alkenes, alkynes, adapted for oral administration effective to reduce or prevent the at least one cardiac channelopathies, $I_{Kr}$ channel inhibition or QT prolongation caused by the drug; and adapted for oral administration effective to reduce or prevent one or more cardiac channelopathies or conditions resulting from irregularities or alterations in cardiac patterns caused by the drug; and measuring the effect of the combination of the lysophosphatidylglycerol and the therapeutically active agent or the drug on the drug-induced channelopathy, wherein the composition reduces or eliminated the channelopathy induced by the therapeutically active agent or the drug.

In one embodiment, the present invention includes a method for preventing or treating at least one of $I_{Kr}$ channel inhibition or QT prolongation arising from administration of an active agent that causes a drug-induced channelopathy in a human or animal subject comprising the steps of: identifying the human or animal subject in need of prevention or treatment of a disease treatable active agent that causes a drug-induced channelopathy; and an amount of a lysophosphatidylglycerol adapted for oral administration effective to reduce or prevent one or more cardiac channelopathies or conditions resulting from irregularities or alterations in cardiac patterns caused by the drug; and administering to the human or animal subject a therapeutically effective amount of an active agent that causes a drug-induced channelopathy, wherein the oral lysophosphatidylglycerol reduces or eliminates the channelopathy induced by the therapeutically active agent. In one aspect, the active agent has previously failed a clinical trial due to drug-induced IKr channel inhibition or QT prolongation. In another aspect, the method further comprises the step of identifying a drug in a clinical trial that failed or has limited clinical use due to drug-induced IKr channel inhibition or QT prolongation side-effects. In another aspect, the drug is selected from Albuterol (salbutamol), Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Crizotinib, Dabrafenib, Dasatinib, Desipramine, Dexmedetomidine, Dexmethylphenidate, Dextroamphetamine (d-Amphetamine), Dihydroartemisinin+piperaquine, Diphenhydramine, Disopyramide, Dobutamine, Dofetilide, Dolasetron, Domperidone, Dopamine, Doxepin, Dronedarone, Droperidol, Ephedrine, Epinephrine (Adrenaline), Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide (Frusemide), Galantamine, Gatifloxacin, Gemifloxacin, Granisetron, Halofantrine, Haloperidol, Hydrochlorothiazide, Ibutilide, Iloperidone, Imipramine (melipramine), Indapamide, Isoproterenol, Isradipine, Itraconazole, Ivabradine, Ketoconazole, Lapatinib, Levalbuterol (levsalbutamol), Levofloxacin, Levomethadyl, Lisdexamfetamine, Lithium, Mesoridazine, Metaproterenol, Methadone, Methamphetamine (methamfetamine), Methylphenidate, Midodrine, Mifepristone, Mirabegron, Mirtazapine, Moexipril/HCTZ, Moxifloxacin, Nelfinavir, Nicardipine, Nilotinib, Norepinephrine (noradrenaline), Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone.

In one embodiment, the present invention includes a method of evaluating a candidate drug, wherein the candidate drug causes a channelopathy, the method comprising: (a) administering an amount of an oral lysophosphatidylglycerol and a candidate drug to a first subset of the patients, and a placebo to a second subset of the patients, wherein the oral liposome or liposome precursor is provided in an amount effective to reduce or prevent one or more cardiac channelopathies or conditions resulting from irregularities or alterations in cardiac patterns caused by the candidate drug; (b) measuring the level of channelopathy from the first and second set of patients; and (c) determining if the combination of the oral liposome or liposome precursors and the candidate drug reduce the drug-induced channelopathy that is statistically significant as compared to any reduction occurring in the subset of patients that took the placebo or to the known drug-induced channelopathy, wherein a statistically significant reduction indicates that the combination of the oral lysophosphatidylglycerol and the candidate drug is useful in treating a disease state while also reducing or eliminating the drug-induced channelopathy. In another aspect, the drug has previously failed a clinical trial due to a drug-induced channelopathy, IKr channel inhibition or QT prolongation. In another aspect, the drug has been withdrawn from the marketplace due to a drug-induced channelopathy, IKr channel inhibition or QT prolongation. In another aspect, the method further comprises the step of repeating steps (a) to (c) after a period of time. In another aspect, the drug is selected from Albuterol (salbutamol), Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Crizotinib, Dabrafenib, Dasatinib, Desipramine, Dexmedetomidine, Dexmethylphenidate, Dextroamphetamine (d-Amphetamine), Dihydroartemisinin+piperaquine, Diphenhydramine, Disopyramide, Dobutamine, Dofetilide, Dolasetron, Domperidone, Dopamine, Doxepin, Dronedarone, Droperidol, Ephedrine, Epinephrine (Adrenaline), Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide (Frusemide), Galantamine, Gatifloxacin, Gemifloxacin, Granisetron, Halofantrine, Haloperidol, Hydrochlorothiazide, Ibutilide, Iloperidone, Imipramine (melipramine), Indapamide, Isoproterenol, Isradipine, Itraconazole, Ivabradine, Ketoconazole, Lapatinib, Levalbuterol (levsalbutamol), Levofloxacin, Levomethadyl, Lisdexamfetamine, Lithium, Mesoridazine, Metaproterenol, Methadone, Methamphetamine (methamfetamine), Methylphenidate, Midodrine, Mifepristone, Mirabegron, Mirtazapine, Moexipril/HCTZ, Moxifloxacin, Nelfinavir, Nicardipine, Nilotinib, Norepinephrine (noradrenaline), Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
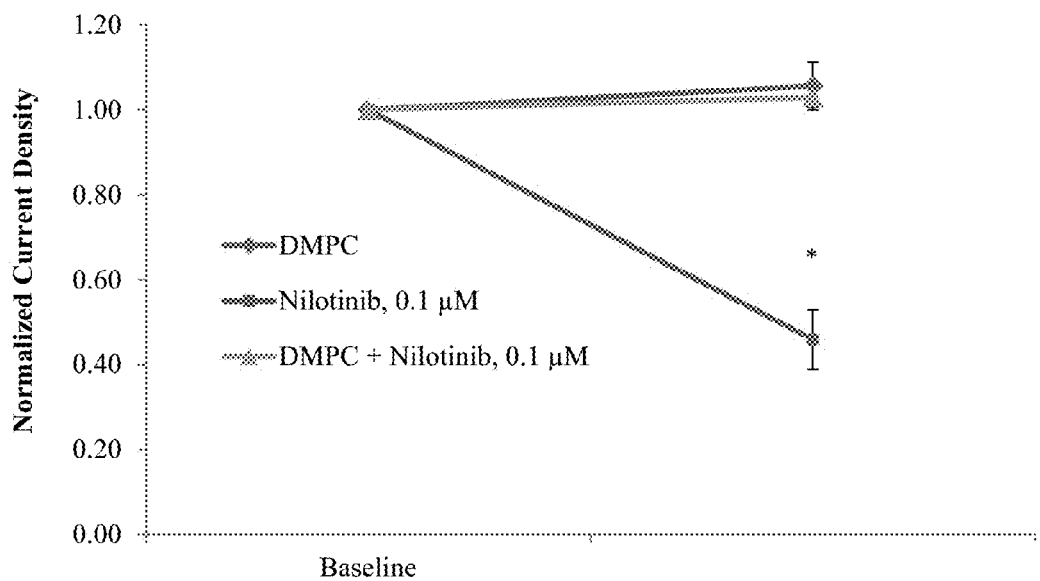
FIG. 1 is a graph that shows the effect of DMPC, DMPC+Nilotinib and Nilotinib on hERG current density from transfected HEK 293 cells.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Non-limiting exemplary lysophosphatidylglycerols for use with the present invention include lysophosphatidylcholines, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine or erucoyl-lysophosphatidylcholine. Asymmetric phosphatidylcholines are referred to as 1-acyl, 2-acyl-sn-glycero-3-phosphocholines, wherein the acyl groups are different from each other. Symmetric phosphatidylcholines are referred to as 1,2-diacyl-sn-glycero-3-phosphocholines. As used herein, the abbreviation "PC" refers to phosphatidylcholine. The phosphatidylcholine 1,2-dimyristoyl-sn-glycero-3-phosphocholine is abbreviated herein as "DMPC." The phosphatidylcholine 1,2-dioleoyl-sn-glycero-3-phosphocholine is abbreviated herein as "DOPC." The phosphatidylcholine 1,2-dipalmitoyl-sn-glycero-3-phosphocholine is abbreviated herein as "DPPC." The single fatty acid chain version of these short or long chain fatty acids are referred to as the "lyso" forms when only a single fatty acid chain is attached to the glyceryl backbone.

In one embodiment, the lysophosphatidylglycerol has a basic structure:

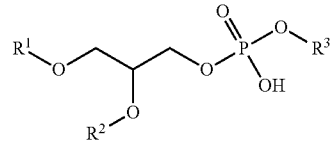

wherein $R^1$ or $R^2$ can be any even or odd-chain fatty acid, and $R^3$ can be H, acyl, alkyl, aryl, amino acid, alkenes, alkynes, and wherein a short chain fatty acid is up to 5 carbons, a medium chain is 6 to 12 carbons, a long chain is 13-21 carbons and a very long chain fatty acid is greater than 22 carbons, including both even and odd chain fatty acids. In one example, the fatty acids have 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55 or long fatty acids, which can be saturated or unsaturated. The present invention can be used with any QT prolonging drug, including but not limited to those listed at: www.crediblemeds.org, Albuterol (salbutamol), Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Crizotinib, Dabrafenib, Dasatinib, Desipramine, Dexmedetomidine, Dexmethylphenidate, Dextroamphetamine (d-Amphetamine), Dihydroartemisinin+piperaquine, Diphenhydramine, Disopyramide, Dobutamine, Dofetilide, Dolasetron, Domperidone, Dopamine, Doxepin, Dronedarone, Droperidol, Ephedrine, Epinephrine (Adrenaline), Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide (Frusemide), Galantamine, Gatifloxacin, Gemifloxacin, Granisetron, Halofantrine, Haloperidol, Hydrochlorothiazide, Ibutilide, Iloperidone, Imipramine (melipramine), Indapamide, Isoproterenol, Isradipine, Itraconazole, Ivabradine, Ketoconazole, Lapatinib, Levalbuterol (levsalbutamol), Levofloxacin, Levomethadyl, Lisdexamfetamine, Lithium, Mesoridazine, Metaproterenol, Methadone, Methamphetamine (methamfetamine), Methylphenidate, Midodrine, Mifepristone, Mirabegron, Mirtazapine, Moexipril/HCTZ, Moxifloxacin, Nelfinavir, Nicardipine, Nilotinib, Norepinephrine (noradrenaline), Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone.

Human ether-a-go-go-related gene (hERG) Potassium channel anti-blockade by liposome and fragments.

Potassium channels conduct the rapid component of the delayed rectifier potassium current, Kir, which is crucial for repolarization of cardiac action potentials. A reduction in hERG currents due to either genetic defects or adverse drug effects can lead to hereditary or acquired long QT syndromes characterized by action potential prolongation, lengthening of the QT interval on the surface ECG, and an increased risk for "torsade de pointes" arrhythmias and sudden death. This undesirable side effect of non-antiarrhythmic compounds has prompted the withdrawal of drugs from the market. Studies on mechanisms of hERG channel inhibition provide significant insights into the molecular factors that determine state-, voltage-, and use-dependency of hERG current block. Mutations altering properties of the high-affinity drug binding site in hERG and its interaction with drug molecules cause current increase and hereditary short QT syndrome with a high risk for life-threatening arrhythmias. (Thomas D1, 2006).

Anatomical Characteristics of the K+ Channel.

The types and distributions of inwardly rectifying potassium (Kir) channels are one of the major determinants of the electrophysiological properties of cardiac myocytes. Inward rectifier potassium (Kir) channels regulate cell excitability and transport of K+ ions across cell membranes.

The potassium channel from *Streptomyces lividans* is an integral membrane protein with sequence similarity to all known K$^+$ channels, particularly in the pore region. X-ray analysis with data to 3.2 angstroms reveals that four identical subunits create an inverted teepee, or cone, cradling the selectivity filter of the pore in its outer end. The narrow selectivity filter is only 12 angstroms long, whereas the remainder of the pore is wider and lined with hydrophobic amino acids. A large water-filled cavity and helix dipoles are positioned so as to overcome electrostatic destabilization of an ion in the pore at the center of the bilayer. Main chain carbonyl oxygen atoms from the K$^+$ channel signature sequence line the selectivity filter, which is held open by structural constraints to coordinate K$^+$ ions but not smaller Na$^+$ ions. The selectivity filter contains two K$^+$ ions about 7.5 angstroms apart. Ion channels exhibit ion selectivity through pore architecture that conducts specific ions. This configuration promotes ion conduction by exploiting electrostatic repulsive forces to overcome attractive forces between K$^+$ ions and the selectivity filter. The architecture of the pore establishes the physical principles underlying selective K$^+$ conduction. (Doyle D A, 1998).

Another member of the inward-rectifier family of potassium channels is the prokaryotic KirBac1.1 channel. The structure of the Kir channel assembly in the closed state, when refined to a resolution of 3.65 angstroms contains a main activation gate and structural elements involved in gating. On the basis of structural evidence, gating involves coupling between the intracellular and membrane domains suggesting that initiation of gating by membrane or intracellular signals represents different entry points to a common mechanistic pathway. (Kuo, A 2003).

Kir channels in the cardiac myocytes may be actively regulated by means of the change in PIP(2) level rather than by downstream signal transduction pathways. The classical inward rectifier K(+) channel), Kir2.1, Kir6.2/SUR2A (ATP-sensitive K(+) channel) and Kir3.1/3.4 (muscarinic K(+) channels) in cardiac myocytes are commonly upregulated by a membrane lipid, phosphatidylinositol 4,5-bisphosphates (PIP(2)). PIP(2) interaction sites appear to be conserved by positively charged amino acid residues and the putative alpha-helix in the C-terminals of Kir channels. PIP(2) level in the plasma membrane is regulated by tagonist stimulation (Takano M I 2003).

Inward rectifier potassium channels are characterized by two transmembrane helices per subunit, plus an intracellular C-terminal domain that controls channel gating in response to changes in concentration of various ligands. Based on the crystal structure of the tetrameric C-terminal domain of Kir3.1, it is possible to build a homology model of the ATP-binding C-terminal domain of Kir6.2. Molecular dynamics simulations are used to probe the dynamics of Kir C-terminal domains and to explore the relationship between their dynamics and possible mechanisms of channel gating. Multiple simulations, each of 10 ns duration, were performed for Kir3.1 (crystal structure) and Kir6.2 (homology model), in both their monomeric and tetrameric forms. The Kir6.2 simulations were performed with and without bound ATP. The results of the simulations reveal comparable conformational stability for the crystal structure and the homology model. There is decrease in conformational flexibility when comparing the monomers with the tetramers, corresponding mainly to the subunit interfaces in the tetramer. The beta-phosphate of ATP interacts with the side chain of K185 in the Kir6.2 model and simulations. The flexibility of the Kir6.2 tetramer is not changed greatly by the presence of bound ATP, other than in two loop regions. Principal components analysis of the simulated dynamics suggests loss of symmetry in both the Kir3.1 and Kir6.2 tetramers, consistent with "dimer-of-dimers" motion of subunits in C-terminal domains of the corresponding Kir channels. This is suggestive of a gating model in which a transition between exact tetrameric symmetry and dimer-of-dimers symmetry is associated with a change in transmembrane helix packing coupled to gating of the channel. Dimer-of-dimers motion of the C-terminal domain tetramer is also supported by coarse-grained (anisotropic network model) calculations. Loss of exact rotational symmetry is suggested to play a role in gating in the bacterial Kir homolog, KirBac1.1, and in the nicotinic acetylcholine receptor channel. (Haider S I, 2005).

Homotetrameric models of three mammalian Kir channels (Kir1.1, Kir3.1, and Kir6.2) have been generated, using the KirBac3.1 transmembrane and rat Kir3.1 intracellular domain structures as templates. All three models were explored by 10 ns molecular dynamics simulations in phospholipid bilayers. Analysis of the initial structures revealed conservation of potential lipid interaction residues (Trp/Tyr and Arg/Lys side chains near the lipid headgroup-water interfaces). Examination of the intracellular domains revealed key structural differences between Kir1.1 and Kir6.2 which may explain the difference in channel inhibition by ATP. The behavior of all three models in the MD simulations revealed that they have conformational stability similar to that seen for comparable simulations of, for example, structures derived from cryoelectron microscopy data. Local distortions of the selectivity filter were seen during the simulations, as observed in previous simulations of KirBac and in simulations and structures of KcsA. These may be related to filter gating of the channel. The intracellular hydrophobic gate does not undergo any substantial changes during the simulations and thus remains functionally closed. Analysis of lipid-protein interactions of the Kir models emphasizes the key role of the M0 (or "slide") helix which lies approximately parallel to the bilayer-water interface and forms a link between the transmembrane and intracellular domains of the channel (Haider S I, 2007).

The potassium-selective transmembrane pore in voltage-activated K+ channels is gated by changes in the membrane potential. Activation gating (opening) occurs in milliseconds and involves a gate at the cytoplasmic side of the pore. Substituting cysteine at a particular position in the last transmembrane region (S6) of the homotetrameric Shaker K+ channel creates metal binding sites at which Cd2+ ions can bind with high affinity. The bound Cd2+ ions form a bridge between the introduced cysteine in one channel subunit and a native histidine in another subunit, and the bridge traps the gate in the open state. These results suggest that gating involves a rearrangement of the intersubunit contacts at the intracellular end of S6. The structure of a bacterial K+ channel shows that the S6 homologs cross in a bundle, leaving an aperture at the bundle crossing. In the context of this structure, the metal ions form a bridge between a cysteine above the bundle crossing and a histidine below the bundle crossing in a neighboring subunit. results suggest that gating occurs at the bundle crossing, possibly through a change in the conformation of the bundle itself (Holmgren M L 2002).

Activated gating in voltage-activated K+ channels are a potassium-selective transmembrane pore gated by changes in the membrane potential. This activation gating (opening) occurs in milliseconds and involves a gate at the cytoplasmic side of the pore. Substituting cysteine at a particular position in the last transmembrane region (S6) of the homotetrameric Shaker K+ channel creates metal binding sites at which Cd2+ ions can bind with high affinity. The bound Cd2+ ions form a bridge between the introduced cysteine in one channel subunit and a native histidine in another subunit, and the bridge traps the gate in the open state. These results suggest that gating involves a rearrangement of the inter-subunit contacts at the intracellular end of S6. The structure of a bacterial K+ channel shows that the S6 homologs cross in a bundle, leaving an aperture at the bundle crossing. In the context of this structure, the metal ions form a bridge between a cysteine above the bundle crossing and a histidine below the bundle crossing in a neighboring subunit. results suggest that gating occurs at the bundle crossing, possibly through a change in the conformation of the bundle itself (Holmgren M L 2002).

Channelopathies

The human ether-à-go-go gene related cardiac tetrameric potassium channel. when mutated can render patients sensitive to over 163 drugs which may inhibit ion conduction and deregulate action potentials. (Credible Meds) Prolongation of the action potential follows effects in the potassium channel. Ion channel active drugs may directly increase the QTc interval, and increase the risk of torsade de point and sudden cardiac death. (Table 1) Exacerbation of cardiomyocyte potassium channel sensitivity to drugs may also be associated with metabolic diseased states including diabetes (Veglio M, 2002) or may be of idiopathic origin.

For these reasons, evaluation of drug effects on cardiomyocyte potassium channel function is a critical step during drug development, and when serious, may be an obstacle to regulatory approval. In whole-cell patch-clamp experiments, curcumin inhibited hERG K$^+$ currents in HEK293 cells stably expressing hERG channels in a dose-dependent manner, with IC$_{50}$ value of 5.55 µM. The deactivation, inactivation and the recovery time from inactivation of hERG channels were significantly changed by acute treatment of 10 µM curcumin. Incubation of 20 µM curcumin for 24 h reduced the HEK293 cell viability. Intravenous injection of 20 mg of curcumin in rabbits did not affect the cardiac repolarization manifested by QTc values. (Hu C W 2012).

However, SignPath Pharma has discovered specific molecules which antagonize QTc prolonging drugs (Helson L, 2002 Ranjan A, 2014, Shopp G, 2014). These molecules are specific liposomes, or components of liposomes which were initially bound to lipophilic drugs to permit intravenous solubility at physiological conditions, and reduce adverse events. The loci of action appears to be in intra-channel ion selectivity or gating site(s) controlling potassium ion movement: a key functional component of regulation of action potentials which lead downstream to myocyte contraction.

The mechanism of human ether-à-go-go related gene channels blocade may be analogous to the effects of externally applied quaternary ammonium derivatives which indirectly may suggest the mechanism of action of the anti-blockading effect of the DMPC/DMPG liposome or its metabolites. The inhibitory constants and the relative binding energies for channel inhibition indicate that more hydrophobic quaternary ammoniums have higher affinity blockade while cation-π interactions or size effects are not a deterministic factor in channel inhibition by quaternary ammoniums. Also hydrophobic quaternary ammoniums either with a longer tail group or with a bigger head group than tetraethylammonium permeate the cell membrane to easily access the high-affinity internal binding site in the gene channel and exert a stronger blockade.

Although these data suggest that the basis for the ameliorating effect liposome, or its components is the higher competitive affinity for binding sites by the, DMPC and DMPG compared to QTc prolonging drugs( ), its constitutive lack of ion transport modulation, i.e. liposome or its fragments do not impede K+ ion transport indicates that By way of explanation, and in no way a limitation of these claims, these data suggest that the basis for the ameliorating effect liposome, or its components, is the higher competitive affinity for binding sites by the DMPC and DMPG compared to QTc prolonging drugs, its constitutive lack of ion transport modulation, i.e., liposome, or its fragments, do not impede K+ ion transport and indicates that the site of the mechanism of DMPC or DMPG protection may be in the selectivity segment of the channel or in the hydration surrounding the ion.

Additionally, based upon these hERG channel data the structures of these liposome components may be informative for designing or selecting other molecules to prevent drug induced cardiac arrhythmias.

This study provides additional information as to the QTc modulating effects by drugs, induced in cardiac myocyte potassium channels, and mitigation by liposomes and liposomal constituents. The latter molecules present an opportunity to probe the K$^+$ channels as targets for pharmacological mitigation of drug-induced channelopathies.

Evaluation of the protective effect of DMPC, DMPG, DMPC/DMPG, LysoPG and LysoPC against hERG inhibition by Nilotinib.

Purpose of the study: The purpose of this study is to evaluate in vitro the protective effect of DMPC, DMPG, DMPC/DMPG, LysoPG and LysoPC on the rapidly activating delayed-rectifier potassium selective current ($I_{Kr}$) generated under normoxic conditions in stably transfected Human Embryonic Kidney cells (HEK 293 cells). This study was designed as a screen and does not require QA involvement (non-GLP-compliant).

Test Articles:
1—DMPC
2—DMPG
3—DMPC/DMPG 90:9
4—14:0 LysoPC

5—14:0 LysoPG
6—DMPC+Nilotinib (0.1 µM)
7—DMPG+Nilotinib (0.1 µM)
8—DMPC/DMPG 90:9+Nilotinib (0.1 µM)
9—14:0 LysoPC+Nilotinib (0.1 µM)
10—14:0 LysoPG+Nilotinib (0.1 µM)

Test System: hERG-expressing HEK 293 transfected cell line. Test performed: Whole-cell patch-clamp current acquisition and analysis. Experimental Temperature: 35±2° C.

Application of Test Articles:

5 minutes of exposure to each concentration in presence of closed circuit perfusion (2 mL/min). 5 minutes for washout periods in presence of a flow-through perfusion (2 mL/min) in addition to a closed circuit perfusion (2 mL/min). The positive control (Nilotinib, 0.05 µg/mL) was added to naive cells obtained from the same cell line and same passage for a period of 5 minutes in presence of a closed circuit perfusion (2 mL/min).

Cells were under continuous stimulation of the pulses protocol throughout the experiments and cell currents were recorded after 5 minutes of exposure to each condition.

Original data acquisition design: Acquisition Rate(s): 1.0 kHz.

Design for acquisition when testing the compound or the vehicle/solvent equivalent:
1 recording made in baseline condition
1 recording made in the presence of concentration 1
Design for acquisition when testing the positive control:
1 recording made in baseline condition
1 recording made in the presence of the positive control
n=number of responsive cells patched on which the whole protocol above could be applied.

Statistical analysis: Statistical comparisons were made using paired Student's t-tests. The currents recorded obtained on day 2, 3 and 4 were statistically compared to the currents recorded on day 1.

The currents recorded after the positive control (nilotinib alone) exposure were compared to the currents recorded in baseline conditions.

Differences were considered significant when p≤0.05.

Exclusion Criteria:
1. Timeframe of drug exposure not respected
2. Instability of the seal
3. No tail current generated by the patched cell
4. No significant effect of the positive control
5. More than 10% variability in capacitance transient amplitude over the duration of the Study.

Effect of the Test Articles on whole-cell $I_{Kr}$ hERG currents. Whole-cell currents elicited during a voltage pulse were recorded in baseline conditions and following the application of the selected concentration of test article. The cells were depolarized for one second from the holding potential (−80 mV) to a maximum value of +40 mV, starting at −40 mV and progressing in 10 mV increments. The membrane potential was then repolarized to −55 mV for one second, and finally returned to −80 mV.

Whole-cell tail current amplitude was measured at a holding potential of −55 mV, following activation of the current from −40 to +40 mV. Current amplitude was measured at the maximum (peak) of this tail current. Current density was obtained by dividing current amplitude by cell capacitance measured prior to capacitive transient minimization.

Current run-down and solvent effect correction. All data points presented in this Study Report have been corrected for solvent effect and time-dependent current run-down. Current run-down and solvent effects were measured simultaneously by applying the experimental design in test-article free conditions over the same time frame as was done with the test article. The loss in current amplitude measured during these so-called vehicle experiments (representing both solvent effects and time-dependent run-down) was subtracted from the loss of amplitude measured in the presence of the test article to isolate the effect of the test article, apart from the effect of the solvent and the inevitable run-down in current amplitude over time.

TABLE 1

Effect of DMPC, DMPC + Nilotinib and Nilotinib on hERG current density from transfected HEK 293 cells.

| | Normalized Current Density | Corrected Normalized Current Density | SEM | p value | n = |
|---|---|---|---|---|---|
| Baseline | 1.000 | 1.000 | n/a | n/a | 3 |
| DMPC | 0.863 | 1.056 | 0.056 | 0.423 | 3 |
| Nilotinib, 0.1 µM | 0.308 | 0.459* | 0.070 | 0.016 | 3 |
| DMPC + Nilotinib, 0.1 µM | 0.836 | 1.029 | 0.023 | 0.328 | 3 |

FIG. 1 is a graph that shows the effect of DMPC, DMPC+Nilotinib and Nilotinib on hERG current density from transfected HEK 293 cells.

TABLE 2

Effect of DMPG, DMPG + Nilotinib and Nilotinib on hERG current density from transfected HEK 293 cells.

| | Normalized Current Density | Corrected Normalized Current Density | SEM | p value | n = |
|---|---|---|---|---|---|
| Baseline | 1.000 | 1.000 | n/a | n/a | 3 |
| DMPG | 0.800 | 0.994 | 0.044 | 0.901 | 3 |
| Nilotinib, 0.1 µM | 0.308 | 0.459* | 0.070 | 0.016 | 3 |
| DMPG + Nilotinib, 0.1 µM | 0.743 | 0.936 | 0.067 | 0.437 | 3 |

Figure 2:
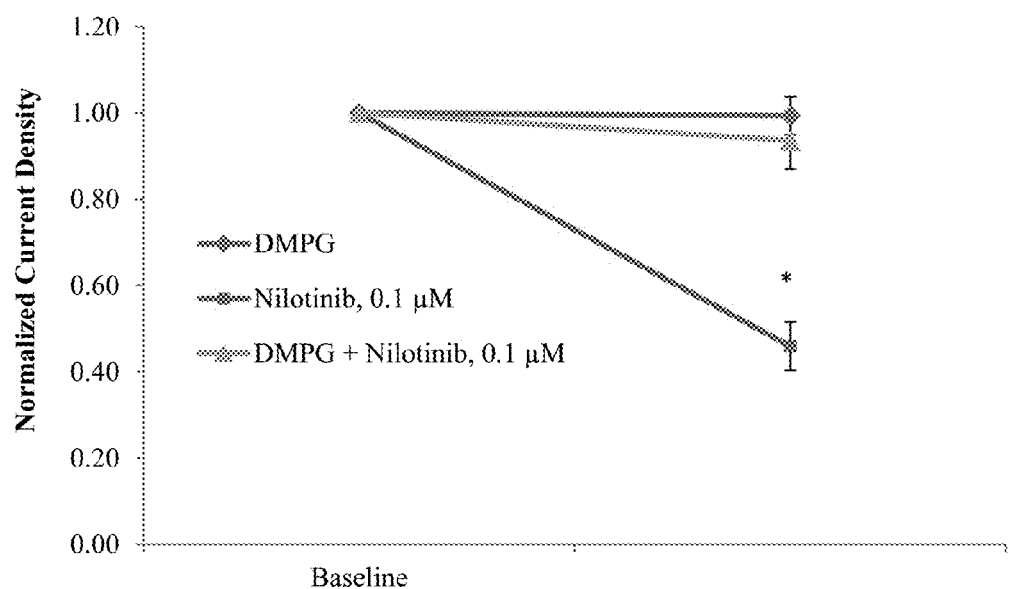
FIG. 2 is a graph that shows the effect of DMPG, DMPG+Nilotinib and Nilotinib on hERG current density from transfected HEK 293 cells.

FIG. 2 is a graph that shows the effect of DMPG, DMPG+Nilotinib and Nilotinib on hERG current density from transfected HEK 293 cells.

TABLE 3

Effect of DMPC/DMPG, DMPC/DMPG + Nilotinib and Nilotinib on hERG current density from transfected HEK 293 cells.

| | Normalized Current Density | Corrected Normalized Current Density | SEM | p value | n = |
|---|---|---|---|---|---|
| Baseline | 1.000 | 1.000 | n/a | n/a | 3 |
| DMPC-DMPG | 0.871 | 1.064 | 0.127 | 0.647 | 4 |
| Nilotinib, 0.1 µM | 0.308 | 0.459* | 0.070 | 0.016 | 3 |
| DMPC/DMPG + Nilotinib, 0.1 µM | 0.773 | 0.966 | 0.098 | 0.754 | 4 |

Figure 3:
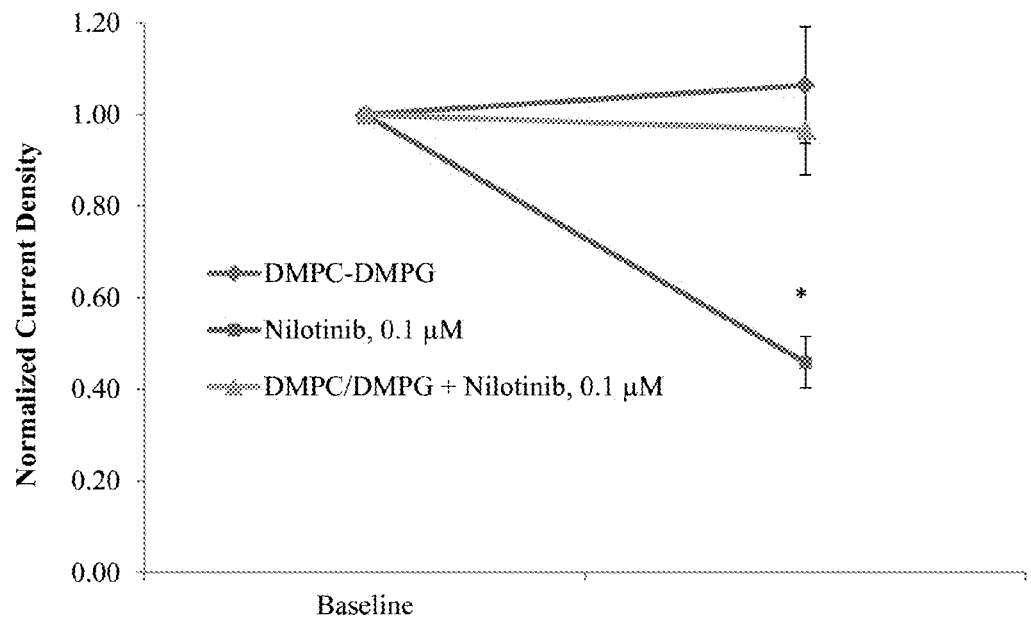
FIG. 3 is a graph that shows the effect of DMPC/DMPG, DMPC/DMPG+Nilotinib and Nilotinib on hERG current density from transfected HEK 293 cells.

FIG. 3 is a graph that shows the effect of DMPC/DMPG, DMPC/DMPG+Nilotinib and Nilotinib on hERG current density from transfected HEK 293 cells.

TABLE 4

Effect of LysoPC, LysoPC + Nilotinib and Nilotinib on hERG
current density from transfected HEK 293 cells.

|  | Normalized Current Density | Corrected Normalized Current Density | SEM | p value | n = |
|---|---|---|---|---|---|
| Baseline | 1.000 | 1.000 | n/a | n/a | 3 |
| LysoPC | 0.647 | 0.840* | 0.040 | 0.028 | 4 |
| Nilotinib, 0.1 μM | 0.308 | 0.459* | 0.070 | 0.016 | 3 |
| LysoPC + Nilotinib, 0.1 μM | 0.865 | 1.097 | 0.055 | 0.553 | 3 |

Figure 4:
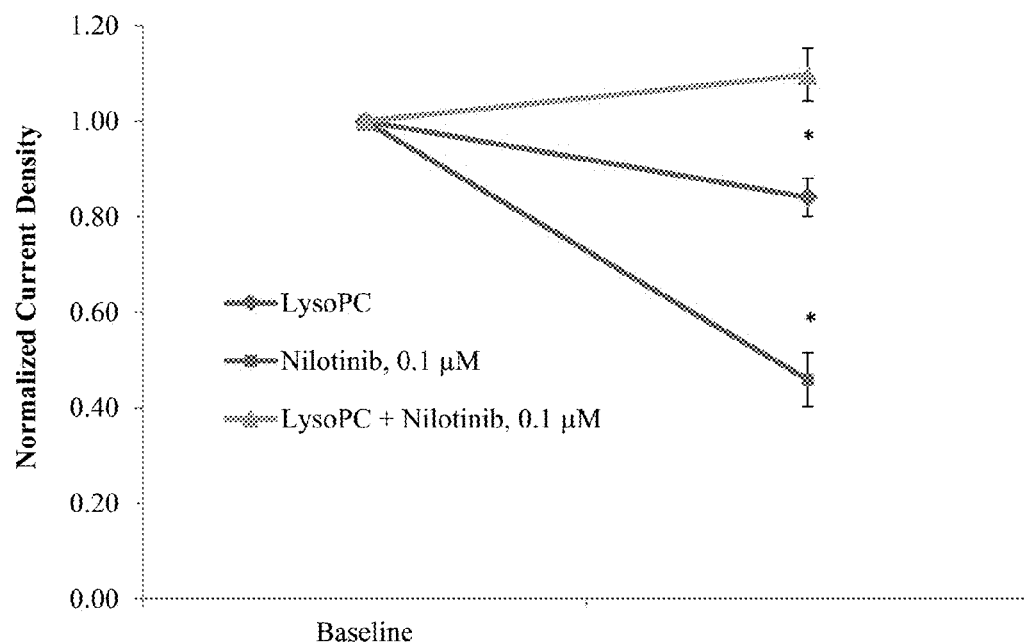
FIG. 4 is a graph that shows the effect of LysoPC, LysoPC+Nilotinib and Nilotinib on hERG current density from transfected HEK 293 cells.

FIG. 4 is a graph that shows the effect of LysoPC, LysoPC+Nilotinib and Nilotinib on hERG current density from transfected HEK 293 cells.

TABLE 5

Effect of LysoPG, LysoPG + Nilotinib and Nilotinib on hERG
current density from transfected HEK 293 cells.

|  | Normalized Current Density | Corrected Normalized Current Density | SEM | p value | n = |
|---|---|---|---|---|---|
| Baseline | 1.000 | 1.000 | n/a | n/a | 3 |
| 14:0 LysoPG, 0.45 μg/mL | 0.930 | 1.124 | 0.128 | 0.435 | 3 |
| Nilotinib, 0.1 μM | 0.308 | 0.459* | 0.070 | 0.016 | 3 |
| 14:0 LysoPG + Nilotinib, 0.1 μM | 0.743 | 0.936 | 0.067 | 0.437 | 3 |

Figure 5:
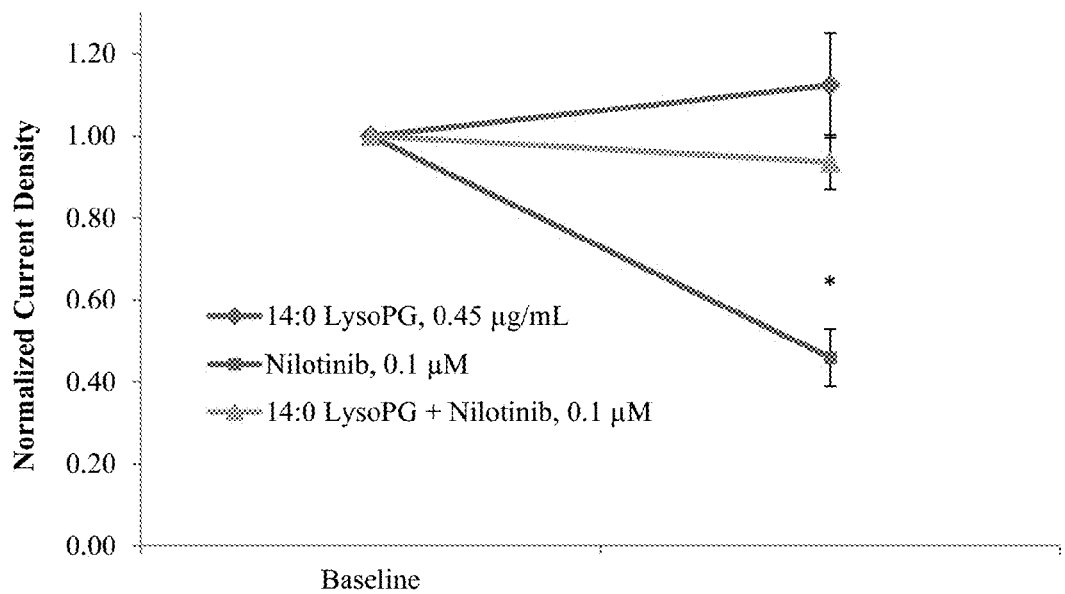
FIG. 5 is a graph that shows the effect of LysoPG, LysoPG+Nilotinib and Nilotinib on hERG current density from transfected HEK 293 cells.

FIG. 5 is a graph that shows the effect of LysoPG, LysoPG+Nilotinib and Nilotinib on hERG current density from transfected HEK 293 cells.

This study aimed at quantifying the protective effect of DMPC, DMPG, DMPC/DMPG, LysoPG and LysoPC against the inhibition of the rapidly activating delayed-rectifier potassium selective current ($I_{Kr}$) generated under normoxic conditions in stably transfected Human Embryonic Kidney (HEK) 293 cells caused by the Nilotinib.

All data points presented in this study have been corrected for solvent effects and time-dependent current run-down. These two parameters were evaluated by applying exactly the same experimental design to the vehicle as that done with the test articles. The currents were measured over the same time course as was done in the presence of the test article. The values obtained, representing both solvent effects and time-dependent run-down, were used to correct the effect of the test articles, if any. This ensures that changes attributable to time or the solvent are not mistakenly attributed to the test articles.

DMPC, DMPG, DMPC/DMPG and LysoPG alone did not cause any inhibition of the hERG tail current density (n=3). LysoPC alone caused 16% of inhibition of the hERG tail current density (n=4).

Nilotinib alone, formulated in DMSO at 0.1 μM, caused 54.1% of inhibition of the hERG tail current (n=3). The inhibition observed is in line with previous data generated in identical conditions, and agrees with reported inhibition values for this compound.

Nilotinib when formulated in an aqueous solution containing DMPC, DMPG, DMPC/DMPC, LysoPG or LysoPC (ratio 1:9) did not cause any inhibition of the hERG tail current.

These data suggest that co-formulating Nilotinib with DMPC, DMPG, DMPC/DMPC, LysoPG and LysoPC protects against hERG inhibition caused by Nilotinib.

In this study, the DMPC+Nilotinib, DMPG+Nilotinib, DMPC/DMPC+Nilotinib, LysoPG+Nilotinib or LysoPC+Nilotinib were all formulated using the same method. The appropriate amount of Nilotinib powder was dissolved in an aqueous solution containing either DMPC, DMPG, DMPC/DMPC, LysoPG or LysoPC (ratio 9:1). The solution was vortexed for 10 minutes before being used in the patch-clamp assay.

In contrast, the Nilotinib used for the cells exposed to Nilotinib alone was dissolved in DMSO. Additional studies were conducted to determine whether the difference in hERG inhibition between DMSO-formulated Nilotinib and lipid-co-formulated Nilotinib resulted from the different formulations (aqueous or DMSO-based).

Steps for the Study:

| Step 1 | Step 2 | Step 3 | Step 4 |
|---|---|---|---|
| Baseline recording | TA* added into the experimental chamber | 5 minutes exposure time | TA recording |

*TA =
1- DMPC (in aqueous solution)
2- DMPG (in aqueous solution)
3- DMPC/DMPG 90:9 (in aqueous solution)
4- 14:0 LysoPC (in aqueous solution)
5- 14:0 LysoPG (in aqueous solution)
6- DMPC + Nilotinib (0.1 μM) (in aqueous solution)
7- DMPG + Nilotinib (0.1 μM) (in aqueous solution)
8- DMPC/DMPG 90:9 + Nilotinib (0.1 μM) (in aqueous solution)
9- 14:0 LysoPC + Nilotinib (0.1 μM) (in aqueous solution)
10- 14:0 LysoPG + Nilotinib (0.1 μM) (in aqueous solution)
11- Nilotinib alone (in DMSO)

Amongst the mechanisms considered to explain the protection of hERG currents were the possibility that DMPC/DMPG or the Lyso-variants quenched the Nilotinib at the moment of formulation, essentially preventing it from getting into the channel at its receptor site. Another possibility was that Nilotinib was less soluble in an aqueous solution, and therefore was incompletely solubilized at 0.1 μM.

To test both hypotheses, Nilotinib was formulated in DMSO and added into the experimental chamber following the addition of the DMPC or DMPG. This was based on the principle that 1—adding DMPC/DMPG alone, followed by DMSO-formulated Nilotinib, would eliminate the possibility of early quenching of Nilotinib by the lysosome; and 2—that DMSO would maintain the solubility of Nilotinib (the "Nilotinib-only" inhibition of hERG was observed when DMSO-formulated Nilotinib was added to the cells).

Steps for the Following Data

| Step 1 | Step 2 | Step 3 | Step 4 | Step 5 | Step 6 |
|---|---|---|---|---|---|
| Baseline recording | DMPC or DMPG added into the experimental chamber | 5 minutes exposure time | DMPC or DMPG recording | Nilotinib in DMSO added into the experimental chamber | DMPC or DMPG + Nilotinib (in DMSO) recording |

TABLE 6

Effect of DMPC, DMPC + Nilotinib, DMPC + Nilotinib (in DMSO) and Nilotinib on hERG current density from transfected HEK 293 cells.

|  | Normalized Current Density | Corrected Normalized Current Density | SEM | p value | n = |
|---|---|---|---|---|---|
| Baseline | 1.000 | 1.000 | n/a | n/a | 3 |
| DMPC | 0.863 | 1.056 | 0.056 | 0.423 | 3 |
| Nilotinib, 0.1 μM | 0.308 | 0.459* | 0.070 | 0.016 | 3 |
| DMPC + Nilotinib, 0.1 μM (Aqueous) | 0.836 | 1.029 | 0.023 | 0.328 | 3 |
| DMPC + Nilotinib (in DMSO), 0.1 μM | 0.164 | 0.358* | 0.020 | 0.019 | 2 |

Figure 6:
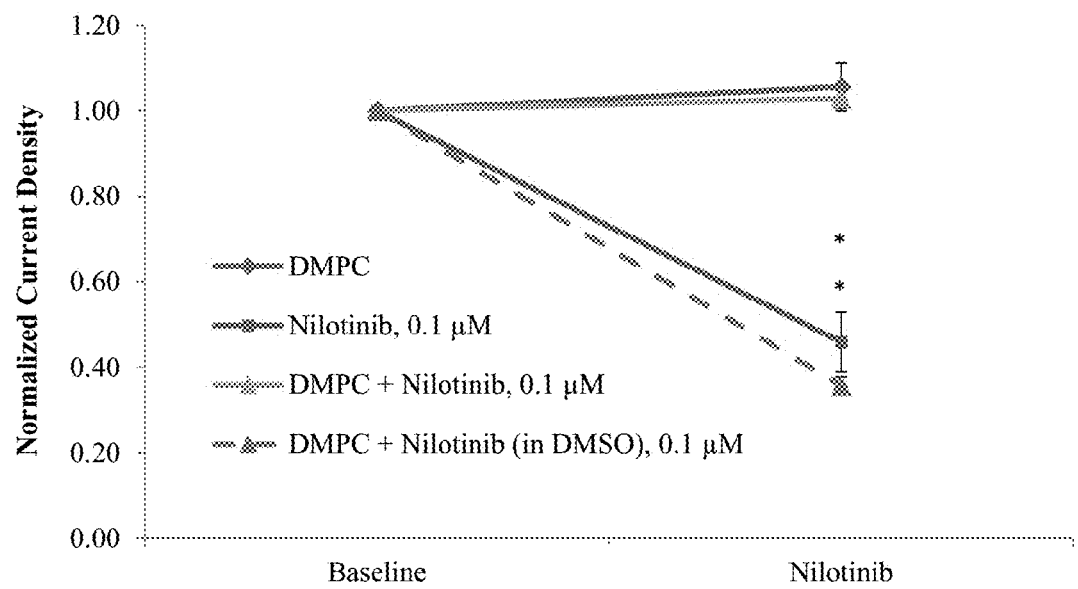
FIG. 6 is a graph that shows the effect of DMPC, DMPC+Nilotinib, DMPC+Nilotinib (in DMSO) and Nilotinib on hERG current density from transfected HEK 293 cells.

FIG. 6 is a graph that shows the effect of DMPC, DMPC+Nilotinib, DMPC+Nilotinib (in DMSO) and Nilotinib on hERG current density from transfected HEK 293 cells.

TABLE 7

Effect of DMPG, DMPG + Nilotinib, DMPG + Nilotinib (in DMSO) and Nilotinib on hERG current density from transfected HEK 293 cells.

|  | Normalized Current Density | Corrected Normalized Current Density | SEM | p value | n = |
|---|---|---|---|---|---|
| Baseline | 1.000 | 1.000 | n/a | n/a | 3 |
| DMPG | 0.800 | 0.994 | 0.044 | 0.901 | 3 |
| Nilotinib, 0.1 μM | 0.308 | 0.459* | 0.070 | 0.016 | 3 |
| DMPG + Nilotinib, 0.1 μM | 0.743 | 0.936 | 0.067 | 0.437 | 3 |
| DMPG + Nilotinib (in DMSO), 0.1 μM | 0.630 | 0.823 | 0.290 | 0.651 | 2 |

Figure 7:
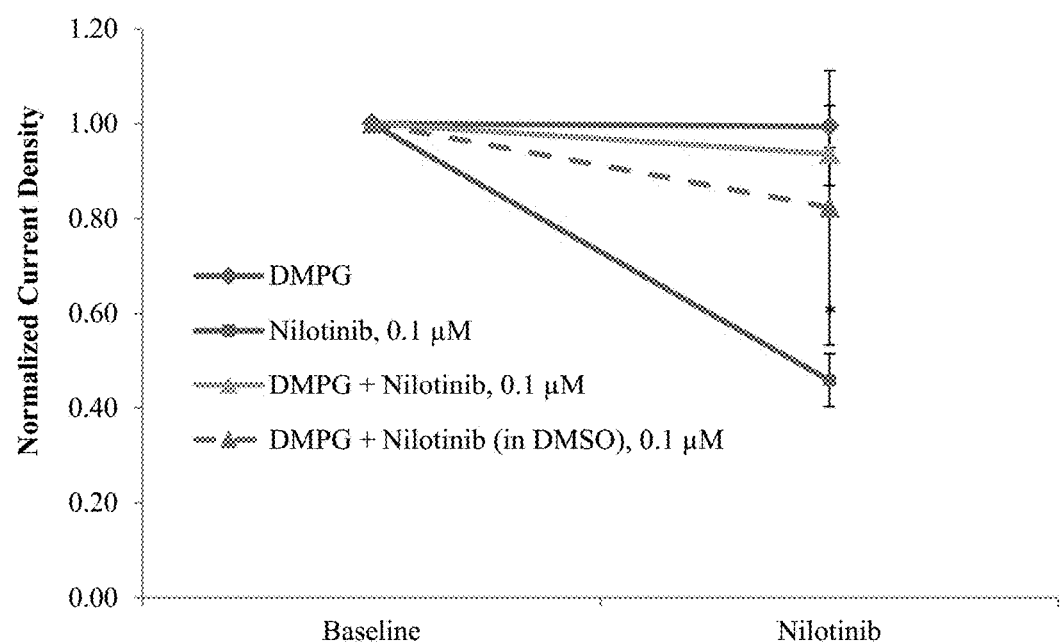
FIG. 7 is a graph that shows the effect of DMPG, DMPG+Nilotinib, DMPG+Nilotinib (in DMSO) and Nilotinib on hERG current density from transfected HEK 293 cells.

FIG. 7 is a graph that shows the effect of DMPG, DMPG+Nilotinib, DMPG+Nilotinib (in DMSO) and Nilotinib on hERG current density from transfected HEK 293 cells.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Patent Publication No. 2010/0004549: System and Method of Serial Comparison for Detection of Long QT Syndrome (LQTS).

U.S. Patent Publication No. 2008/0255464: System and Method for Diagnosing and Treating Long QT Syndrome.

U.S. Patent Publication No. 2007/0048284: Cardiac Arrhythmia Treatment Methods.

U.S. Patent Publication No. 2001/00120890: Ion Channel Modulating Activity I.

What is claimed is:

1. A composition for preventing one or more cardiac channelopathies, irregularities, or alterations in cardiac patterns caused by an active agent or a drug in a human or animal subject consisting of:
   a therapeutically effective amount of the active agent or the drug, wherein the active agent or drug causes one or more cardiac channelopathies, irregularities, or alterations in cardiac patterns; and
   an amount of a lysophosphatidylglycerol in the form of empty liposomes adapted for oral administration effective to reduce or prevent one or more cardiac channelopathies or conditions resulting from irregularities or alterations in cardiac patterns caused by the active agent or drug, wherein the lysophosphatidylglycerol includes at least one of a lysophosphatidylcholine, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine or erucoyl-lysophosphatidylcholine.

2. The composition of claim 1, wherein the lysophosphatidylglycerol include at least one or 1-Myristoyl-2-Hydroxy-snGlycero-3-Phosphocholine (DMPC), 1,2-Dimyristoyl-sn-glycero-3-phospho-rac-(1-glycerol) (DMPG), DMPC/DMPG, 1-myristoyl-2-hydroxy-sn-glycero-3-phospho-(1'-rac-glycerol) (LysoPG), or 1-myristoyl-2-hydroxy-sn-glycero-3-phosphocholine (LysoPC).

3. The composition of claim 1, wherein the lysophosphatidylglycerol is defined further as a short chain fatty acid is up to 5 carbons, a medium chain is 6 to 12 carbons, a long chain is 13-21 carbons and a very long chain fatty acid is greater than 22 carbons, including both even and odd chain fatty acids.

4. The composition of claim 1, wherein the lysophosphatidylglycerol has 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55 or more carbons, which are saturated or unsaturated.

5. The composition of claim 1, wherein the cardiac channelopathy or the condition resulting from the irregularity or alteration in the cardiac pattern is inhibition of an ion channel responsible for the delayed-rectifier K+ current in the heart, polymorphic ventricular tachycardia, prolongation of the QTc, LQT2, LQTS, or torsades de pointes.

6. The composition of claim 1, wherein the composition is used for the treatment or prevention of prolongation of the IKr channel inhibition or QT prolongation induced by administration of the active agent or drug used in the treatment of cardiac, allergic, or cancer related diseases.

7. The composition of claim 1, wherein the active agent drug is selected from at least one of crizotinib, nilotinib, terfenadine, astemizole, gripafloxacin, terodilene, droperidole, lidoflazine, levomethadyl, sertindoyle or cisapride.

8. The composition of claim 1, wherein the active agent drug is provided enterally, parenterally, intravenously, intraperitoneally, or orally.

9. The composition of claim 1, wherein the drug is selected from Albuterol (salbutamol), Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Crizotinib, Dabrafenib, Dasatinib, Desipramine, Dexmedetomidine, Dexmethylphenidate, Dextroamphetamine (d-Amphetamine), Dihydroartemisinin+piperaquine, Diphenhydramine, Disopyramide, Dobutamine, Dofetilide, Dolasetron, Domperidone, Dopamine, Doxepin, Dronedarone, Droperidol, Ephedrine, Epinephrine (Adrenaline), Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide (Frusemide), Galantamine, Gatifloxacin, Gemifloxacin, Granisetron, Halofantrine, Haloperidol, Hydrochlorothiazide, Ibutilide, Iloperidone, Imipramine (melipramine), Indapamide, Isoproterenol, Isradipine, Itraconazole, Ivabradine, Ketoconazole, Lapatinib, Levalbuterol (levsalbutamol), Levofloxacin, Levomethadyl, Lisdexamfetamine, Lithium, Mesoridazine, Metaproterenol, Methadone, Methamphetamine (methamfetamine), Methylphenidate, Midodrine, Mifepristone, Mirabegron, Mirtazapine, Moexipril/HCTZ, Moxifloxacin, Nelfinavir, Nicardipine, Nilotinib, Norepinephrine (noradrenaline), Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone.

10. A composition for preventing or treating a diseases with an active agent or drug that causes one or more adverse reactions arising from administration of an active agent or drug in a human that causes at least one of cardiac channelopathies, IKr channel inhibition or QT prolongation consisting of:
   a therapeutically effective amount of the active agent or the drug, wherein the active agent or drug causes the at least one of cardiac channelopathies, IKr channel inhibition or QT prolongation; and
   an amount of a lysophosphatidylglycerol with a basic structure:

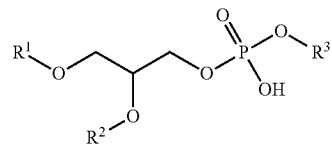

wherein R1 or R2 can be any even or odd-chain fatty acid, and R3 can be H, acyl, alkyl, aryl, amino acid, alkenes, alkynes, in the form of empty liposomes adapted for oral administration effective to reduce or prevent the at least one cardiac channelopathies, IKr channel inhibition or QT prolongation caused by the drug, wherein the lysophosphatidylglycerol includes at least one of a lysophosphatidylcholine, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine or erucoyl-lysophosphatidylcholine.

11. The composition of claim 10, wherein the liposome or liposome precursor are selected from at least one or 1-Myristoyl-2-Hydroxy-snGlycero-3-Phosphocholine (DMPC), 1,2-Dimyristoyl-sn-glycero-3-phospho-rac-(1-glycerol) (DMPG), DMPC/DMPG, 1-myristoyl-2-hydroxy-sn-glycero-3-phospho-(1'-rac-glycerol) (LysoPG), or 1-myristoyl-2-hydroxy-sn-glycero-3-phosphocholine (LysoPC).

12. The composition of claim 10, wherein the short chain fatty acid is up to 5 carbons, a medium chain is 6 to 12 carbons, a long chain is 13-21 carbons and a very long chain fatty acid is greater than 22 carbons, including both even and odd chain fatty acids.

13. The composition of claim 10, wherein the short chain fatty acid has 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55 or more carbons, which are saturated or unsaturated.

14. The composition of claim 10, wherein the cardiac channelopathy or the condition resulting from the irregularity or alteration in the cardiac pattern is inhibition of an ion channel responsible for the delayed-rectifier K+ current in the heart, polymorphic ventricular tachycardia, prolongation of the QTc, LQT2, LQTS, or torsades de pointes.

15. The composition of claim 10, wherein the composition is used for the treatment or prevention of prolongation of the IKr channel inhibition or QT prolongation induced by administration of one or more drugs used in the treatment of cardiac, allergic, or cancer related disease.

16. The composition of claim 10, wherein the one or more active agents is selected from at least one of crizotinib, nilotinib, terfenadine, astemizole, gripafloxacin, terodilene, droperidole, lidoflazine, levomethadyl, sertindoyle or cisapride.

17. The composition of claim 10, wherein the active agent or drug is provided enterally, parenterally, intravenously, intraperitoneally, or orally.

18. The composition of claim 10, wherein the drug is selected from Albuterol (salbutamol), Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Crizotinib, Dabrafenib, Dasatinib, Desipramine, Dexmedetomidine, Dexmethylphenidate, Dextroamphetamine (d-Amphetamine), Dihydroartemisinin+piperaquine, Diphenhydramine, Disopyramide, Dobutamine, Dofetilide, Dolasetron, Domperidone, Dopamine, Doxepin, Dronedarone, Droperidol, Ephedrine, Epinephrine (Adrenaline), Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide (Frusemide), Galantamine, Gatifloxacin, Gemifloxacin, Granisetron, Halofantrine, Haloperidol, Hydrochlorothiazide, Ibutilide, Iloperidone, Imipramine (melipramine), Indapamide, Isoproterenol, Isradipine, Itraconazole, Ivabradine, Ketoconazole, Lapatinib, Levalbuterol (levsalbutamol), Levofloxacin, Levomethadyl, Lisdexamfetamine, Lithium, Mesoridazine, Metaproterenol, Methadone, Methamphetamine (methamfetamine), Methylphenidate, Midodrine, Mifepristone, Mirabegron, Mirtazapine, Moexipril/HCTZ, Moxifloxacin, Nelfinavir, Nicardipine, Nilotinib, Norepinephrine (noradrenaline), Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone.

* * * * *